United States Patent
Roopenian et al.

(10) Patent No.: US 10,457,719 B2
(45) Date of Patent: Oct. 29, 2019

(54) ANTIBODIES AND FC FUSION PROTEIN MODIFICATIONS WITH ENHANCED PERSISTENCE OR PHARMACOKINETIC STABILITY IN VIVO AND METHODS OF USE THEREOF

(75) Inventors: Derry Roopenian, Salisbury Cove, ME (US); Gregory Christianson, Seal Cove, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 532 days.

(21) Appl. No.: 12/678,494

(22) PCT Filed: Sep. 17, 2008

(86) PCT No.: PCT/US2008/076581
§ 371 (c)(1),
(2), (4) Date: Apr. 14, 2010

(87) PCT Pub. No.: WO2009/097017
PCT Pub. Date: Aug. 6, 2009

(65) Prior Publication Data
US 2010/0209424 A1    Aug. 19, 2010

Related U.S. Application Data

(60) Provisional application No. 60/994,428, filed on Sep. 18, 2007.

(51) Int. Cl.
| | | |
|---|---|---|
| A61K 47/68 | (2017.01) | |
| A61K 47/55 | (2017.01) | |
| C07K 16/00 | (2006.01) | |
| A61K 47/54 | (2017.01) | |
| A61K 39/00 | (2006.01) | |

(52) U.S. Cl.
CPC ............ *C07K 16/00* (2013.01); *A61K 47/557* (2017.08); *A61K 47/6835* (2017.08); *A61K 2039/505* (2013.01); *C07K 2317/21* (2013.01); *C07K 2317/24* (2013.01); *C07K 2317/72* (2013.01); *Y02A 50/396* (2018.01)

(58) Field of Classification Search
CPC .......................... C07K 16/00; C07K 2317/21; C07K 2317/72; C07K 2317/94; C07K 2317/24; A61K 47/557; A61K 47/6835; A61K 2039/505
See application file for complete search history.

(56) References Cited

U.S. PATENT DOCUMENTS

| | | | |
|---|---|---|---|
| 5,283,342 A | 2/1994 | Gustavson et al. | |
| 6,217,869 B1 * | 4/2001 | Meyer et al. | ............... 424/178.1 |
| 6,277,375 B1 | 8/2001 | Ward | |
| 2003/0104578 A1 | 6/2003 | Ballance | |
| 2004/0001827 A1 | 1/2004 | Dennis | |

FOREIGN PATENT DOCUMENTS

| | | |
|---|---|---|
| WO | 2004/108885 A | 12/2004 |
| WO | WO 2006/118772 A2 * | 11/2006 |
| WO | 2006/130834 A | 12/2006 |

OTHER PUBLICATIONS

Stancovski et al., Proceedings of the National Academy of Science USA 88: 8691-8695 (Year: 1991).*
Cochran et al., J. Immunol. Meth. 287: 147-158 (Year: 2004).*
Firan, M. et al., International Immunology, 13(8):993-1002 (2001). "The MHC class I-related receptor, FcRn, plays an essential role in the maternofetal transfer of gamma-globulin in humans.".
Khawli, L.A. et al., Cancer Biotherapy and Radiopharmaceuticals, 17(4):359-370 (2002). "Pharmacokinetic characteristics and biodistribution of radioiodinated chimeric TNT-1, -2, and -3 monoclonal antibodies after chemical modification with biotin.".
Lance Martin, W.L. et al., Molecular Cell, 7(4):867-877 (2001). "Crystal structure at 2.8 ANG of an FcRn/heterodimeric Fc complex: Mechanism of pH-dependent binding.".
Petkova, S.B. et al., International Immunology, 18(12):1759-1769 (2006). "Enhanced half-life of genetically engineered human IgG1 antibodies in a humanized FcRn mouse model: potential application in humorally mediated autoimmune disease.".
Sharifi, J. et al., Quarterly Journal of Nuclear Medicine, 42(4):242-249 (1998). "Improving monoclonal antibody pharmacokinetics via chemical modification.".
Shields, R.L. et al., Journal of Biological Chemistry, 276(9):6591-6604 (2001). "High resolution mapping of the binding site on human IgG1 for FcgammaRI, FcgammaRII, FcgammaRIII, and FcRn and design of IgG1 variants with improved binding to the FcgammaR.".
Wang, Z. et al., Cancer Biotherapy and Radiopharmaceuticals, 18(3):365-375 (2003). "Biotinylation, pharmacokinetics, and extracorporeal adsorption of humanized MAB 111IN-MN14 using an avidin-affinity column in rats.".
Ali et al., "Transferrin Trojan Horses as a Rational Approach for the Biological Delivery of Therapeutic Peptide Domains", J Biol Chem, 274(34): 24066-24073 (1999).
Ashkenazi et al., "Immunoadhesins as research tools and therapeutic agents", Current Opinion in Immunology, (1997). 9:195-200.
Carter, "Potent antibody therapeutics by design", Nature Reviews Immunology, 6: 343-357 (2006).
Chapman, "PEGylated antibodies and antibody fragments for improved therapy: a review", Advanced Drug Delivery, 54: 531-545 (2002).
Dennis et al., "Albumin Binding as a General Strategy for Improving the Pharmacokinetic of Proteins", J Biol Chem, 277(38): 35035-35043 (2002).
Duttaroy et al., "Development of a Long Acting Insulin Analgo Using Albumin Fusion Technology": , Diabetes, 54: 251-258 (2005).
Elliot et al., "Enhancement of therapeutic protein in vivo activities through glycoengineering", Nat Bioltechnol, 21: 414-421 (2003).

(Continued)

*Primary Examiner* — Phuong Huynh
(74) *Attorney, Agent, or Firm* — Nixon Peabody LLP; David S. Resnick; Mark J. FitzGerald

(57) ABSTRACT

In certain embodiments, this present invention provides antibodies and Fc fusion proteins with enhanced pharmacokinetics, such as biotinylated antibodies or biotinylated Fc fusion polypeptides.

3 Claims, 15 Drawing Sheets

Specification includes a Sequence Listing.

(56) References Cited

OTHER PUBLICATIONS

Ghetie et al., "Increasing the serum persistence of an IgG fragment by random mutagenesis", Nat Biotechnol, 15: 637-640 (1997).
Ghetie et al., "Multiple Roles for the Major Histocompatibility Complex Class I-Related Receptor FcRn", Annu Rev Immunol, 18: 739-766 (2000).
Ghetie et al., "Transcytosis and Catabolism of Antibody", Immunol Res, 25(2): 97-113 (2002).
Jain et al., "Engineering antibodies for clinical application", Trends in Biotechnology, 25(7): 307-316 (2007).
Keyt et al., "A faster-acting and more potent form of tissue plasminogen activator", Proc Natl Acad Sci USA, 91: 3670-3674 (1994).
Levy et al., "Cellulose-binding domains Biotechnological applications", Biotechnology Advances, 20: 191-213 (2002).
Melder et al., "Pharmacokinetics and in vitro and in vivo antiOtumor response of an interleukin-2-human serum albumin fusion protein in mice", Cancer Immunol Immunother, 54: 535-547 (2005).
Mimura et al., The influence of glycosylation on the thermal stability and effector function expression of human IgG1-Fc: properties of a series of truncated glycoforms:, Molecular Immunology 37: 697-706 (2000).
Osborn et al., "Albutropin: a growth hormone-albumin fusion with improved pharmacokinetics and pharmacodynamics in rats and monkeys"., European Journal of Pharmacology 456: 149-158 (2002).
Osborn et al., "Pharmacokinetic and Pharmacodynamic Studies of a Human Serum Albumin-Interferon-a Fusion Protein in Cynomolgus Monkeys", Journal of Pharmcology and Expermintal Therapeutics, 303(2): 540-548 (2002).
Raju et al., "Glycosylation in the Fc fomain of TgG increases resistance to proteolytic cleavage by papain", Biochem Biophys Res Commun, 341: 797-803 (2006).
Raju et al., "Fc Glycans Terminated with N-Acetylglycosamine Residues Increase Antibody Resistance to Papain", Biotechnol Prog, 23: 964-971 (2007).
Roopenian et al., "The MHC Class I-LIke IgG Receptor Controls Perinatal IgG Transport, IgG Homeostasis, and Fate of IgG-Fc-Coupled Drugs", J Immunol, 170: 3528-3533 (2003).
Roopenian et al., "FcRn: the neonatal Fc receptor comes of age", Nat Rev Immunol, 7: 715-725 (2007).
Sinclair et al., Glycoengineering: The Effect of Glycosylation on the Properties of Therapeutics Proteins, Journal of Pharmaceutical Sciences, 94(8): 1626-1635 (2005).
Smith et al., "Prolonged in Vivo Residence Times of Antibody Fragments Associated with Albumin", Bioconjugate Chem, 12: 750-756 (2001).
Sung et al., "An IFN-B-Albumin Fusion Protein That Displays Improved Pharmacokinetic and Pharmacodynamic Properties in Nonhuman Primates", Journal of Interferon & Cytokine Research, 23: 25-36 (2003).
Umana et al., "Engineered glycoforms of an antineuroblastoma IgG1 with optimized antibody-dependent cellular cytotoxic activity", Nat Biotechnol, 17: 176-180 (1999).
Vaccaro et al., "Engineering the Fc region of immunoglobulin G to modulate in vivo antibody levels", Nat Biotechnol, 23(10): 1283-1288 (2005).
Veronese et al., "PEGylation, successful approach to drug delivery", Drug Discovery Today,10(21): 1451-1458 (2005).
Waldmann et al., "Metabolism of Immunoglobulins", Progr Allergy, 13: 1-110 (1969).
Yeh et al., "Design of yeast-secreted albumin derivatives for human therapy: Biological and antiviral properties of a serum albumin-CD4 genetic conjugate", Proc Natl Acad Sci USA, 89: 1904-1908 (1992).

\* cited by examiner

```
                      SEQUENCE LISTING

<160> NUMBER OF SEQ ID NOS: 18

<210> SEQ ID NO 1
   <211> LENGTH: 18
   <212> TYPE: PRT
   <213> ORGANISM: Homo sapiens

<400> SEQUENCE: 1

Phe Asn Trp Tyr Val Asp Gly Val Glu Val His Asn Ala Lys Thr Lys
   1               5                   10                  15

Pro Arg

<210> SEQ ID NO 2
   <211> LENGTH: 18
   <212> TYPE: PRT
   <213> ORGANISM: Homo sapiens

<400> SEQUENCE: 2

Phe Lys Trp Tyr Val Asp Gly Val Glu Val His Asn Ala Lys Thr Lys
   1               5                   10                  15

Pro Arg

<210> SEQ ID NO 3
   <211> LENGTH: 12
   <212> TYPE: PRT
   <213> ORGANISM: Homo sapiens

<400> SEQUENCE: 3

Val Ser Asn Lys Ala Leu Pro Ala Pro Ile Glu Lys
   1               5                   10

<210> SEQ ID NO 4
   <211> LENGTH: 18
   <212> TYPE: PRT
   <213> ORGANISM: Artificial
   <220> FEATURE:
   <223> OTHER INFORMATION: Cysteine for lysine substitution of human Fc
         domain peptide sequence

<400> SEQUENCE: 4

Phe Asn Trp Tyr Val Asp Gly Val Glu Val His Asn Ala Cys Thr Lys
   1               5                   10                  15

Pro Arg

<210> SEQ ID NO 5
   <211> LENGTH: 18
   <212> TYPE: PRT
   <213> ORGANISM: Artificial
   <220> FEATURE:
   <223> OTHER INFORMATION: Cysteins for lysine substitution of human Fc
         domain peptide sequence
```

```
<400> SEQUENCE: 5

Phe Asn Trp Tyr Val Asp Gly Val Glu Val His Asn Ala Lys Thr Cys
1               5                   10                  15

Pro Arg

<210> SEQ ID NO 6
<211> LENGTH: 18
<212> TYPE: PRT
<213> ORGANISM: Artificial
<220> FEATURE:
<223> OTHER INFORMATION: Cysteins for lysine substitution of human Fc
      domain peptide sequence

<400> SEQUENCE: 6

Phe Asn Trp Tyr Val Asp Gly Val Glu Val His Asn Ala Cys Thr Cys
1               5                   10                  15

Pro Arg

<210> SEQ ID NO 7
<211> LENGTH: 18
<212> TYPE: PRT
<213> ORGANISM: Artificial
<220> FEATURE:
<223> OTHER INFORMATION: Cysteins for lysine substitution of human Fc
      domain peptide sequence

<400> SEQUENCE: 7

Phe Cys Trp Tyr Val Asp Gly Val Glu Val His Asn Ala Lys Thr Lys
1               5                   10                  15

Pro Arg

<210> SEQ ID NO 8
<211> LENGTH: 18
<212> TYPE: PRT
<213> ORGANISM: Artificial
<220> FEATURE:
<223> OTHER INFORMATION: Cysteins for lysine substitution of human Fc
      domain peptide sequence

<400> SEQUENCE: 8

Phe Lys Trp Val Tyr Asp Gly Val Glu Val His Asn Ala Cys Thr Lys
1               5                   10                  15

Pro Arg

<210> SEQ ID NO 9
<211> LENGTH: 18
<212> TYPE: PRT
<213> ORGANISM: Artificial
<220> FEATURE:
<223> OTHER INFORMATION: Cysteins for lysine substitution of human Fc
      domain peptide sequence

<400> SEQUENCE: 9

Phe Lys Trp Tyr Val Asp Gly Val Glu Val His Asn Ala Lys Thr Cys
1               5                   10                  15

Pro Arg

<210> SEQ ID NO 10
<211> LENGTH: 18
<212> TYPE: PRT
<213> ORGANISM: Artificial
<220> FEATURE:
<223> OTHER INFORMATION: Cysteins for lysine substitution of human Fc
```

```
                          domain peptide sequence

<400> SEQUENCE: 10

Phe Cys Trp Tyr Val Asp Gly Val Glu Val His Asn Ala Cys Thr Lys
1               5                   10                  15

Pro Arg

<210> SEQ ID NO 11
<211> LENGTH: 18
<212> TYPE: PRT
<213> ORGANISM: Artificial
<220> FEATURE:
<223> OTHER INFORMATION: Cysteins for lysine substitution of human Fc
      domain peptide sequence

<400> SEQUENCE: 11

Phe Cys Trp Tyr Val Asp Gly Val Glu Val His Asn Ala Lys Thr Cys
1               5                   10                  15

Pro Arg

<210> SEQ ID NO 12
<211> LENGTH: 18
<212> TYPE: PRT
<213> ORGANISM: Artificial
<220> FEATURE:
<223> OTHER INFORMATION: Cysteins for lysine substitution of human Fc
      domain peptide sequence

<400> SEQUENCE: 12

Phe Lys Trp Tyr Val Asp Gly Val Glu Val His Asn Ala Cys Thr Cys
1               5                   10                  15

Pro Arg

<210> SEQ ID NO 13
<211> LENGTH: 18
<212> TYPE: PRT
<213> ORGANISM: Artificial
<220> FEATURE:
<223> OTHER INFORMATION: Cysteins for lysine substitution of human Fc
      domain peptide sequence

<400> SEQUENCE: 13

Phe Cys Trp Tyr Val Asp Gly Val Glu Val His Asn Ala Cys Thr Cys
1               5                   10                  15

Pro Arg

<210> SEQ ID NO 14
<211> LENGTH: 12
<212> TYPE: PRT
<213> ORGANISM: Artificial
<220> FEATURE:
<223> OTHER INFORMATION: Cysteins for lysine substitution of human Fc
      domain peptide sequence

<400> SEQUENCE: 14

Val Ser Asn Cys Ala Leu Pro Ala Pro Ile Glu Lys
1               5                   10

<210> SEQ ID NO 15
<211> LENGTH: 12
<212> TYPE: PRT
<213> ORGANISM: artificial
<220> FEATURE:
<223> OTHER INFORMATION: Cysteins for lysine substitution of human Fc
      domain peptide sequence
```

<400> SEQUENCE: 15

Val Ser Asn Lys Ala Leu Pro Ala Pro Ile Glu Cys
1               5                   10

<210> SEQ ID NO 16
<211> LENGTH: 12
<212> TYPE: PRT
<213> ORGANISM: Artificial
<220> FEATURE:
<223> OTHER INFORMATION: Cysteins for lysine substitution of human Fc
      domain peptide sequence

<400> SEQUENCE: 16

Val Ser Asn Cys Ala Leu Pro Ala Pro Ile Glu Cys
1               5                   10

<210> SEQ ID NO 17
<211> LENGTH: 330
<212> TYPE: PRT
<213> ORGANISM: Homo sapiens

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 225
<212> TYPE: PRT
<213> ORGANISM: Artificial
<220> FEATURE:
<223> OTHER INFORMATION: Chimeric human IgG1 Fc fragment and murine CDR

<400> SEQUENCE: 18

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

ANTIBODIES AND FC FUSION PROTEIN MODIFICATIONS WITH ENHANCED PERSISTENCE OR PHARMACOKINETIC STABILITY IN VIVO AND METHODS OF USE THEREOF

CROSS REFERENCE TO RELATED APPLICATIONS

This application is a 35 U.S.C. § 371 National Phase Entry Application of International Application No. PCT/US2008/076581 filed Sep. 17, 2008, which designates the U.S., and which claims the benefit of priority under 35 U.S.C. § 119(e) of U.S. Provisional Application No. 60/994,428 filed Sep. 18, 2007, the contents of which are incorporated herein by reference in its entirety.

GOVERNMENT SUPPORT

Work described herein was funded, in whole or in part, by National Institutes of Health Grant Number NIH R01DK056597. The United States government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 18, 2012, is named 060636061231.txt and is 12,288 bytes in size.

FIELD OF THE INVENTION

The present invention relates to enhancing the in vivo persistence and stability of antibodies and Fc fusion polypeptides by biotinylation, and methods of uses therein.

BACKGROUND OF THE INVENTION

Antibodies have been known since before the 20th century to play an important role in immunological protection against infectious organisms. The immune system cells that produce antibodies are B-lymphocytes. There are four major classes: immunoglobulin M (IgM), IgG, IgA, and IgE, but IgG is by far the most prevalent class, comprising about 90% of all antibodies in adults. Each class of antibody has a specific role in immunity, including primary and secondary immune responses, antigen inactivation and allergic reactions. IgG is the only class of antibody that can pass the placental barrier, thus providing protection from pathogens before the newborn's immune system develops. Antibody molecules have two ends. One end is the antigen-specific binding portion of an antibody referred to as Fab, which is highly variable and engenders each antibody with the capacity to bind a specific molecular shape. The other end, referred to as Fc, has sequence and structural similarities within a class and confers the ability to bind to receptors on immunological cells that specify the effector function of antibodies. In a perfectly operating immune system, the diverse specificities of the antigen specific receptor engenders the host with a diverse repertoire of antibodies with the ability to bind to a wide array of foreign infectious microorganisms, the result being destruction of the microbe and gain of immunity.

Most molecules, including IgM and IgE antibodies, only remain a short amount of time in the circulation because such proteins are constantly being taken up by the process of fluid phase endocytosis. This constitutive biological process results in the targeting of the endocytic material through the early endosomal compartment to the lysosomes, where the material is efficiently destroyed by a process referred to as catabolism (reviewed in (Waldmann and Strober, 1969)). It has been established that antibodies of the IgG class have a greatly extended half-life in circulation. This increase is the direct result of a unique Fc receptor for IgG molecules, the neonatal Fc receptor or FcRn, which is also known as Fcgrt or FcRp (reviewed in (Ghetie and Ward, 2000, 2002; Roopenian and Akilesh, 2007)). FcRn greatly slows the catabolism of the IgG molecules by binding them in the acidic early endosomal cellular compartment before they enter the lysosomal degradation pathway, causing instead the recycling of the IgG antibodies back to the cell surface where they are released in the neutral extracellular pH environment into the circulation (reviewed in (Ghetie and Ward, 2000, 2002; Roopenian and Akilesh, 2007)). The net effect is a substantial increase in the half-life of IgG antibodies in circulation compared with those of proteins that lack the Fc region and are not rescued and recycled by the FcRn mediated pathway. Several investigators have indirectly demonstrated such a protective effect by coupling the Fc region of IgG to different polypeptides to improve stability of the polypeptides. In addition, the use of immunoglobulin-like domains in increasing the stability and longevity of pharmaceutical compositions for therapeutic and diagnostic purposes has also been suggested (U.S. Pat. No. 6,277,375).

A key element in drug development is to achieve adequate circulating half-lives, which impact dosing, drug administration and efficacy. Many approaches have been undertaken with the aim to increase the half-life of biotherapeutics. Small proteins below 60 kD are cleared rapidly by the kidney and therefore do not reach their target. This means that high doses are needed to reach efficacy. The modifications currently used to increase the half-life of proteins in circulation include: PEGylation; conjugation or genetic fusion with proteins, e.g., transferrin (WO06096515A2), albumin, growth hormone (US2003104578AA); conjugation with cellulose (Levy and Shoseyov, 2002); conjugation or fusion with Fc fragments; glycosylation and mutagenesis approaches (Carter, 2006).

In the case of PEGylation, polyethylene glycol (PEG) is conjugated to the protein, which can be for example a plasma protein, antibody or antibody fragment. The first studies regarding the effect of PEGylation of antibodies were performed in the 1980s. The conjugation can be done either enzymatically or chemically and is well established in the art (Chapman, 2002; Veronese and Pasut, 2005). With PEGylation the total size can be increased, which reduces the chance of renal filtration. PEGylation further protects from proteolytic degradation and slows the clearance from the blood. Further, it has been reported that PEGylation can reduce immunogenicity and increase solubility. The improved pharmacokinetics by the addition of PEG is due to several different mechanisms: increase in size of the molecule, protection from proteolysis, reduced antigenicity, and the masking of specific sequences from cellular receptors. In the case of antibody fragments (Fab), a 20-fold increase in plasma half-life has been achieved by PEGylation (Chapman, 2002).

To date there are several approved PEGylated drugs, e.g., PEG-interferon alpha2b (PEG-INTRON) marketed in 2000 and alpha2a (Pegasys) marketed in 2002. A PEGylated antibody fragment against TNF alpha, called Cimzia or Certolizumab Pegol, was filed for FDA approval for the treatment of Crohn's disease in 2007 and has been approved on Apr. 22, 2008. A limitation of PEGylation is the difficulty in synthesizing long monodisperse species, especially when PEG chains over 1000 kD are needed. For many applications, polydisperse PEG with a chain length over 10000 kD is used, resulting in a population of conjugates having different length PEG chains, which need extensive analytics to ensure equivalent batches between productions. The different length of the PEG chains may result in different biological activities and therefore different pharmacokinetics. Another limitation of PEGylation is a decrease in affinity or activity as it has been observed with alpha-interferon Pegasys, which has only 7% of the antiviral activity of the native protein, but has improved pharmacokinetics due to the enhanced plasma half-life.

Another approach is to conjugate the drug with a long lived protein, e.g. albumin, which is 67 kD and has plasma half-life of 19 days in human (Dennis et al., 2002). Albumin is the most abundant protein in plasma and is involved in plasma pH regulation, but also serves as a carrier of substances in plasma. In the case of CD4, increased plasma half-life has been achieved after fusing it to human serum albumin (Yeh et al., 1992). Other examples for fusion proteins are insulin, human growth hormone, transferrin and cytokines (Ali et al., 1999; Duttaroy et al., 2005; Melder et al., 2005; Osborn et al., 2002a; Osborn et al., 2002b; Sung et al., 2003) and see (US2003104578A1, WO06096515A2, and WO07047504A2, herein incorporated in entirety by reference).

The effect of glycosylation on plasma half-life and protein activity has also been extensively studied. In the case of tissue plasminogen activator (tPA) the addition of new glycosylation sites decreased the plasma clearance, and improved the potency (Keyt et al., 1994). Glycoengineering has been successfully applied for a number of recombinant proteins and immunoglobulins (Elliott et al., 2003; Raju and Scallon, 2007; Sinclair and Elliott, 2005; Umana et al., 1999). Further, glycosylation influences the stability of immunoglobulins (Mimura et al., 2000; Raju and Scallon, 2006).

Another molecule used for fusion proteins is the Fc fragment of an IgG (Ashkenazi and Chamow, 1997). The Fc fusion approach has been utilized, for example in the Trap Technology developed by Regeneron (e.g. IL1 trap and VEGF trap). The use of albumin to extend the half-life of peptides has been described in US2004001827A1. Positive effects of albumin have also been reported for Fab fragments and scFv-HSA fusion protein (Smith et al., 2001). It has been demonstrated that the prolonged serum half-life of albumin is due to a recycling process mediated by the FcRn (Anderson et al., 2006; Chaudhury et al., 2003; Smith et al., 2001).

Another strategy is to use directed mutagenesis techniques targeting the interaction of immunoglobulins to their receptor to improve binding properties, i.e. affinity maturation in the Fc region. With an increased affinity to FcRn a prolonged half-life can be achieved in vivo (Ghetie et al., 1997; Hinton et al., 2006; Jain et al., 2007; Petkova et al., 2006a; Vaccaro et al., 2005). However, affinity maturation strategies require several rounds of mutagenesis and testing. This takes time, is costly and is limited by the number of amino acids that when mutated result in prolonged half-lives. Therefore, simple alternative approaches are needed to improve the in vivo half-life of biotherapeutics. Therapeutics with extended half-lifes in vivo are especially important for the treatment of chronic diseases, autoimmune disorders, inflammatory, metabolic, infectious, and eye diseases, and cancer, especially when therapy is required over a long time period. Accordingly, a need still exists for the development of therapeutic agents (e.g., antibodies and Fc fusion proteins) with enhanced persistence and half-lives in circulation, in order to reduce the dosage and/or the frequency of injections of a variety of therapeutic agents.

SUMMARY OF THE INVENTION

The present invention provides, in part, novel treatments and methods of use therein by increasing the half-life of circulating antibodies and Fc fusion polypeptides. The invention is based upon the novel finding that biotinylation of the Fc domain of an antibody or a fusion polypeptide comprising an Fc domain increases the serum half-life of the biotinylated antibody or fusion polypeptide.

Accordingly, the invention provides a method of treating a disorder in a subject in need thereof, comprising administering to the subject an effective amount of an antibody preparation comprising an antibody molecule conjugated to a biotin moiety.

In one embodiment, the biotin moiety is conjugated to the antibody molecule in an amount sufficient to increase the half-life of the antibody molecule in vivo, relative to the half-life of a corresponding antibody molecule that does not comprise a biotin moiety.

In one embodiment, the antibody preparation comprises a monoclonal antibody preparation.

In another embodiment, the antibody preparation comprises a polyclonal antibody preparation. In a further embodiment, the polyclonal antibody preparation consists essentially of a polyclonal population of antibodies specific for a single target molecule. In another further embodiment, the polyclonal antibody preparation comprises a polyclonal population of antibodies specific for a plurality of different molecules. In a further embodiment, the polyclonal antibody preparation is a pooled preparation isolated from a plurality of humans.

In one embodiment, the antibody molecule is a human antibody, humanized antibody, primatized antibody, chimeric antibody, antigen-binding protein comprising a Fc domain, antibody linked to another functional moiety, radiolabeled antibody, a chemolabeled antibody, fusion protein comprising an antibody, Fc domain comprising fusion polypeptide, or fragment thereof. In one embodiment, the antibody molecule is a human immunoglobulin G (IgG) molecule. In a further embodiment, the antibody molecule is selected from the group consisting of IgG1, IgG2, IgG3, and IgG4.

In one embodiment, the antibody molecule comprises a human Fc domain that is bound by the human FcRn receptor. In one embodiment, the antibody molecule is not an antibody that binds the human FcRn receptor as an antigen.

In one embodiment, the antibody comprises a human Fc domain, and the biotin moiety is covalently conjugated to the human Fc domain. In one embodiment, the biotin moiety is covalently conjugated to the CH2—CH3-hinge region, and/or hinge region of the human Fc domain. In a further embodiment, the biotin moiety is covalently conjugated to an amino acid residue. In a further embodiment, the amino acid residue is a lysine. In a preferred embodiment, the biotin moiety is covalently conjugated to a solvent exposed lysine within the human Fc domain sequence FNWYVDGVEVHNAKTKPR (SEQ ID NO:1), FKWYVDGVEVHNAKTKPR (SEQ ID NO:2), or VSNKALPAPIEK (SEQ ID NO:3). In one embodiment, the amino acid residue is a cysteine. In a preferred embodiment, the biotin moiety is covalently conjugated to a cysteine residue that has been genetically engineered onto the Fc domain. In one embodiment, the amount of biotin moiety conjugation to the antibody is at a ratio of at least 2 biotin moiety molecules per antibody molecule.

In one embodiment, the subject is a mammal. In a preferred embodiment, the subject is a human.

In one embodiment, the disorder is a cancer, an inflammatory disease, an infectious disease, a neurodegenerative disease, a metabolic disease, an autoimmune disease, or an immunodeficiency. In a preferred embodiment, the disorder can be treated by antibody therapy. In a preferred embodiment, the disorder can be treated using IVIg therapy. In one embodiment, the disorder requires an allogeneic bone marrow transplant or a transplant. In one further embodiment, the cancer is leukemia, lymphoma, prostate cancer, melanoma, breast cancer, ovarian cancer, head and neck cancer, or colon cancer. In one further embodiment, the autoimmune disease is rheumatoid arthritis, psoriasis, allergy, Kawasaki's disease, idiopathic thrombocytopenic purpura, multiple sclerosis, Guillain-Barre syndrome, Systemic Lupus Erythematosus, myasthenia gravis, or pemphigus. In one further embodiment, the immunodeficiency is hypogammaglobulinemia. In one further embodiment, the inflammatory disease is inflammatory bowel disease, chronic obstructive pulmonary disease, atherosclerosis or osteoarthritis.

In one embodiment, the disorder is caused by a toxin. In one further embodiment, the toxin is a botulism toxin or a snake venom toxin. In one embodiment, the disorder is caused by exposure to a virus. In one further embodiment, the virus is a Hepatitis A virus, Hepatitis B virus, Variola virus, Rabies virus, Ebola virus, herpes simplex virus, varicella zoster virus, Epstein-Barr virus, tick-borne encephalitis, or a cytomegalovirus. In one embodiment, the disorder is caused by exposure to a bacterium. In one further embodiment, the bacterium is *Bacillus anthracis*.

Accordingly, the invention provides a method of treating a disorder in a subject in need thereof, the method comprising administering to the subject an effective amount of Fc fusion polypeptide comprising a human Fc domain fused to a heterologous fusion partner polypeptide, wherein said human Fc domain comprises a conjugated biotin moiety.

In one embodiment, the biotin moiety is conjugated to the Fc fusion polypeptide in an amount sufficient to increase the half-life of the Fc fusion polypeptide in vivo relative to the half-life of a corresponding Fc fusion polypeptide that does not comprise a biotin moiety.

In one embodiment, the human Fc domain is a human IgG Fc domain. In a further embodiment, the human Fc domain is selected from the group consisting of IgG1, IgG2, IgG3, and IgG4.

In one embodiment, the biotin moiety is covalently conjugated to the human Fc domain of the Fc fusion polypeptide. In one embodiment, the biotin moiety is covalently conjugated to the CH2—CH3-hinge region, and/or hinge region of the human Fc domain. In one embodiment, the biotin moiety is covalently conjugated to an amino acid residue. In one embodiment, the amino acid residue is a lysine. In a preferred embodiment, the biotin moiety is covalently conjugated to a solvent exposed lysine within the human Fc domain sequence FNWYVDGVEVHNAKTKPR (SEQ ID NO: 1), FKWYVDGVEVHNAKTKPR (SEQ ID NO: 2), or VSNKALPAPIEK (SEQ ID NO: 3). In one embodiment, the amino acid residue is a cysteine. In a preferred embodiment, the biotin moiety is covalently conjugated to a cysteine residue that has been genetically engineered onto the Fc domain. In one embodiment, the amount of biotin moiety conjugation to the Fc fusion polypeptide is at a ratio of at least 1 biotin moiety molecule per Fc monomer of the Fc fusion polypeptide.

In one embodiment, the disorder is a cancer, an inflammatory disease, a metabolic disease, an autoimmune disease, an immunodeficiency, a neurodegenerative disease, or an eye disorder. In one embodiment, the subject is a mammal. In one preferred embodiment, the subject is a human.

Accordingly, in another aspect, the invention provides an Fc domain-containing fusion polypeptide, wherein said Fc domain comprises a conjugated biotin moiety, and wherein said Fc domain-containing fusion polypeptide has an increased half-life in vivo relative to the half-life of a corresponding Fc domain-containing fusion polypeptide that does not comprise a biotin moiety.

In one embodiment, the Fc domain comprises a human Fc domain. In one embodiment, the Fc domain consists essentially of a human Fc domain. In one embodiment, the Fc domain consists of a human Fc domain.

In one embodiment, the human Fc domain of the Fc domain-containing fusion polypeptide is a human IgG Fc domain. In a further embodiment, the human Fc domain is selected from the group consisting of the human Fc domains of IgG1, IgG2, IgG3, and IgG4.

In one embodiment, the biotin moiety is covalently conjugated to the human Fc domain of the Fc fusion polypeptide. In one embodiment, the biotin moiety is covalently conjugated to the CH2—CH3-hinge region, and/or hinge region of the human Fc domain of the Fc fusion polypeptide. In one embodiment, the biotin moiety is covalently conjugated to an amino acid residue in the human Fc domain of the Fc fusion polypeptide. In a further embodiment, the biotin moiety is covalently conjugated to a lysine. In a preferred embodiment, the biotin moiety is covalently conjugated to a solvent exposed lysine within the human Fc domain sequence FNWYVDGVEVHNAKTKPR (SEQ ID NO: 1), FKWYVDGVEVHNAKTKPR (SEQ ID NO: 2), or VSNKALPAPIEK (SEQ ID NO: 3) of the Fc fusion polypeptide. In one embodiment, the amino acid residue is a cysteine. In a preferred embodiment, the biotin moiety is covalently conjugated to a cysteine residue that has been genetically engineered onto the Fc domain.

In one embodiment, the amount of biotin moiety conjugation to the antibody is at a ratio of at least 1 biotin moiety molecule per Fc domain monomer.

Accordingly, one aspect of the invention provides an antibody preparation, comprising antibodies specific for a plurality of antigens, said antibodies comprising conjugated biotin, and wherein said antibodies are isolated from a human donor.

In one embodiment, the antibodies comprising conjugated biotin have increased serum half-life relative to antibodies of a preparation lacking said biotin. In certain embodiments, the antibodies comprising conjugated biotin have improved pharmacokinetics relative to antibodies of a preparation lacking said biotin. In one embodiment, the antibodies are pooled from a group of human individuals. In certain embodiments, the human individuals are immunized against or immune to a specific antigen. In certain embodiments, the antibody preparation comprises a pharmaceutically acceptable carrier.

Accordingly, one aspect of the invention provides methods for the delivery of a therapeutic antibody or fusion polypeptide across an epithelial layer, the method comprising administering to a subject in need thereof, an antibody or fusion polypeptide comprising an Fc domain, wherein the Fc domain comprises conjugated biotin, and wherein the biotinylated antibody or fusion polypeptide is delivered across the epithelial barrier with increased effectiveness relative to an antibody or fusion polypeptide lacking biotinylation of the Fc domain.

In certain specific embodiments, the biotinylated antibodies and Fc fusion polypeptides of the present invention more efficiently traverse epithelial layers. In a further embodiment, the epithelial layers include the respiratory, intestinal, corneal, or olfactory epithelial layers. In another specific embodiment, the epithelial layer is an endothelial layer. In a more specific embodiment, the endothelial layer is a blood vessel or lymphatic vessel endothelial layer.

Accordingly, in one embodiment, a method is provided for the delivery of a therapeutic antibody or fusion polypeptide across a feto-maternal organ, the method comprising administering to a subject in need thereof, an antibody or fusion polypeptide comprising an Fc domain, wherein the Fc domain comprises conjugated biotin, and wherein the biotinylated antibody or fusion polypeptide is delivered across the feto-maternal organ with increased effectiveness relative to an antibody or fusion polypeptide lacking biotinylation of the Fc domain. In a specific embodiment, the feto-maternal organ is the placenta.

DETAILED DESCRIPTION OF THE INVENTION

Figure 1:
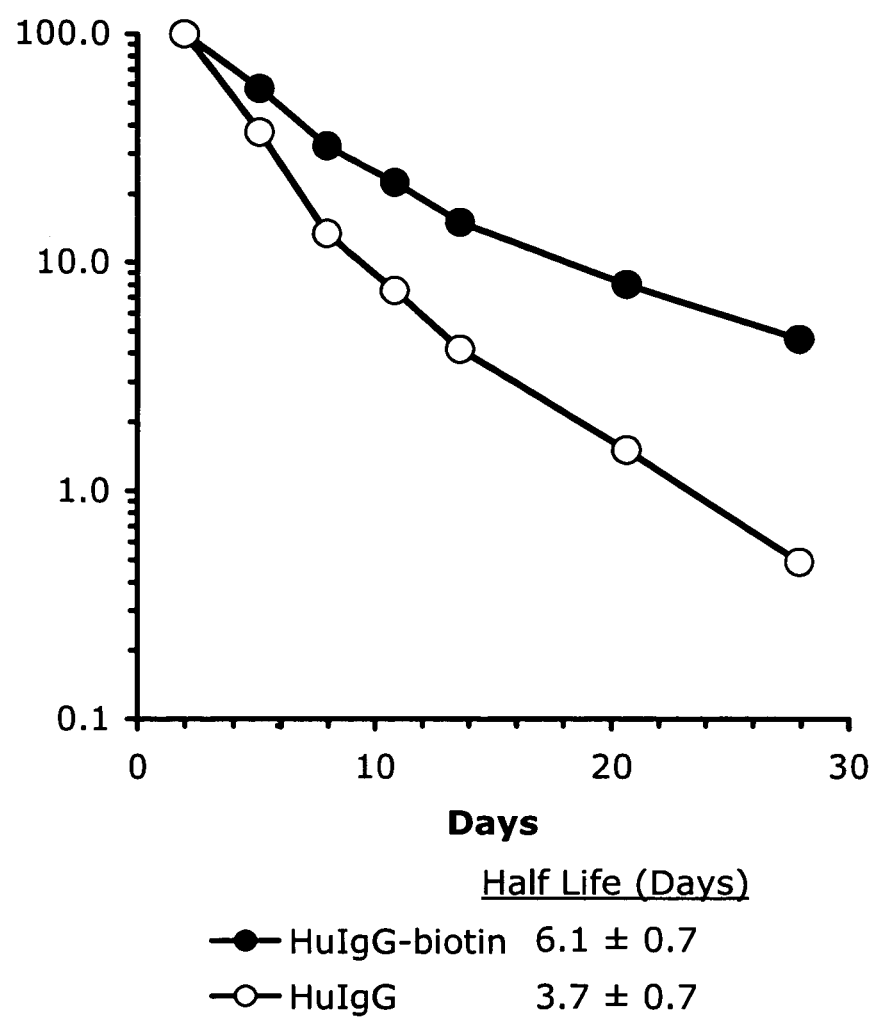
FIG. 1 shows determination of the plasma half-life for biotinylated human (h)IgG (HuIgG-biotin) compared to unmodified human IgG (HuIgG) with the biotinylated hIgG being 6.1 days versus 3.7 days for the unmodified hIgG. The half-life of biotinylated hIgG and unmodified hIgG was determined in C57BL/6 mFcRn−/− hFcRn +/Tg Line 276 transgenic mice expressing the human FcRn receptor while lacking the mouse FcRn receptor. The filled circles are the data points from treatment with biotinylated hIgG, and the open circles from unmodified hIgG.

Certain aspects of the present invention are based, at least in part, on the discovery that biotinylation of an antibody, immunoglobulin, or Fc fusion polypeptide significantly extends its serum half-life relative to the non-biotinylated antibody, immunoglobulin, or Fc fusion polypeptide. Although not wishing to be bound by any particular mechanism or theory, it is believed that the enhanced stability of the biotinylated antibody, immunoglobulin, or Fc fusion polypeptide is dependent on expression of the MHC class I-related receptor FcRn (also referred to as FcRp or Fcgrt). Furthermore, it is known that the human FcRn is very stringent regarding its specificity and binds human Fc, but not mouse, rat, bovine, or sheep Fc. The FcRn can bind to two sites of the IgG (Sanchez et al., 1999; Schuck et al., 1999; West A. P. and Bjorkman, 2000). Mouse IgGs do not bind efficiently to human FcRn and therefore have a short half life in humans (Frodin et al., 1990). In contrast, mouse FcRn binds IgG from every species analyzed (Ober et al., 2001).

Most serum proteins have a short serum half-life (about 1-2 days). However, two types of serum proteins, albumin and antibodies of the IgG class, have greatly extended serum half-lives. For example, most subclasses of IgG have a half-life of about 10-20 days in humans. The Fc region of IgG is required for this extension of half-life. Thus, truncated IgG polypeptides carrying only the Fc region also show such extended serum half-life. Moreover, when the Fc region is fused with a fusion partner (e.g., a biologically active protein), this Fc fusion protein shows an extended serum half-life due to its interaction with FcRn. The mechanism by which FcRn extends the serum half-life of IgG and IgG Fc fusion proteins is well established (Ghetie and Ward, 2000, 2002; Roopenian and Akilesh, 2007). FcRn is localized in the endosomal compartments of many cell types, including vascular endothelium. Serum proteins are constantly being endocytosed and directed to the early endosomal vesicles. FcRn is harbored primarily in this acidified vesicle. In this acidified environment, the Fc region binds FcRn, and the IgG/FcRn complex is then recycled either apically or basolaterally back to the plasma membrane, whereupon exposure to the neutral pH 7.2 extracellular environment results in its release into the circulation. In contrast, other endocytosed proteins that do not bind FcRn are not rescued, and thus continue though the endosomal route to catabolic elimination, resulting in their short half-life. The biochemical mechanism by which the Fc region of IgG binds FcRn in an acidic environment is well understood. The CH2—CH3-hinge region of the Fc region contains solvent exposed histidine residues, which when protonated, engage residues on FcRn with sufficient affinity to permit IgG to exploit the FcRn recycling pathway to escape catabolic elimination.

Modified Antibodies

An object of the present invention is to provide methods and compositions for treating a disorder in a subject, comprising administering to the subject an effective amount of an antibody molecule comprising a biotin moiety. Accordingly in one embodiment, the biotin moiety is conjugated to the antibody molecule in an amount sufficient to increase the half-life of the antibody molecule in vivo relative to the half-life of a corresponding antibody molecule that does not comprise a biotin moiety. In a preferred embodiment, the antibody molecule comprising a biotin moiety comprises an Fc fragment that is capable of binding to the human FcRn receptor. In a preferred embodiment, the antibody molecule comprising a biotin moiety is not an antibody that specifically recognizes the human FcRn receptor as an antigen.

As used herein, the term "antibody" refers to an intact immunoglobulin or to a monoclonal or polyclonal antigen-binding fragment with the Fc (crystallizable fragment) region or FcRn binding fragment of the Fc region, referred to herein as the "Fc fragment" or "Fc domain". Antigen-binding fragments may be produced by recombinant DNA techniques or by enzymatic or chemical cleavage of intact antibodies. Antigen-binding fragments include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The Fc domain includes portions of two heavy chains contributing to two or three classes of the antibody. The Fc domain may be produced by recombinant DNA techniques or by enzymatic (e.g. papain cleavage) or via chemical cleavage of intact antibodies.

An immunoglobulin is typically a tetrameric molecule. As used herein, the term "immunoglobulin" refers to one or more chains of the tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). In human, there are in addition four IgG (IgG1, IgG2, IgG3 and IgG4) and two IgA subtypes present. The classification is done according to differences in their heavy chain constant domains (for review see Janeway C A, Jr. et al (2001), Immunobiology, 5th ed.; Pier G B, Lyczak J B, Wetzler L M (2004), Immunology, Infection, and Immunity, ASM Press ISBN1-55581-246-5, both herein incorporated in entirety by reference). The variable regions of each light/heavy chain pair form the antibody binding site such that an intact natural immunoglobulin has two binding sites.

Immunoglobulin chains exhibit the same general structure: they include relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol., 1997, 196:901-917; Chothia et al. Nature, 1989, 342:878-883 (1989).

The antibody comprising a biotin moiety may be an IgG, an IgM, an IgE, an IgA or an IgD molecule. In a preferred embodiment, the antibody molecule comprising a biotin moiety is an IgG, and more preferably is of the IgG1, IgG2, IgG3, or IgG4 subtype. The class and subclass of antibodies may be determined by any method known in the art, for example, by using antibodies that are specific for a particular class and subclass of antibody. Such antibodies are available commercially. The class and subclass can be determined by ELISA and Western Blots, as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

Antibodies are a major class of biopharmaceuticals. Antibodies for therapeutic purposes are often produced from a cell line (e.g. CHO cells, the hamster line BHK21, the human PER.C6 cell line, COS, NIH 3T3, BHK, HEK, 293, L929, MEL, JEG-3, murine lymphoid cells (including NS0 and Sp2/0-Ag 14)), including hybridomas, and are usually a single clone of a specific antibody. Antibodies used for therapeutic purposes are classified as murine, chimeric, humanized or fully human antibodies and are produced by recombinant methods. A "murine antibody" is a full mouse antibody and has only limited use in humane due to its short half-life in circulation and its high immunogenicity. A "chimeric antibody" is a genetically engineered antibody, which contains both mouse and human sequences. The ratio is approximately 33% mouse contribution and 67% human contribution. Usually the variable domains are murine and the constant region including the Fc fragment is derived from a human IgG.

A "humanized antibody" is a genetically engineered antibody, wherein the mouse content is reduced to about 5-10%. In such cases, the six CDRs of the heavy and light chains and a limited number of structural amino acids of the murine monoclonal antibody are grafted by recombinant technology to the CDR-depleted human IgG scaffold. A fully human antibody or human antibody describes antibodies, which are made in humanized mice resulting in antibodies that do not contain any mouse sequences, or made in vitro using phage libraries or ribosome display or alternatively are obtained from human donors. In certain embodiments, chimeric, humanized or primatized (CDR-grafted) antibodies, comprising portions derived from different species or fully human antibodies, are also encompassed by the present invention as target molecules to be biotinylated. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023; Boss et al., U.S. Pat. No. 4,816,397; Boss et al., European Patent No. 0,120,694; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., BioTechnology, 10: 1455-1460 (1992), regarding primatized antibody. See, e.g., Ladner et al., U.S. Pat. No. 4,946,778; and Bird, R. E. et al., Science, 242: 423-426 (1988)), regarding single chain antibodies.

In addition, functional fragments of antibodies, including fragments of chimeric, humanized, or primatized or fully human antibodies can be biotinylated according to the present invention. Functional fragments of the subject antibodies retain at least one binding and one Fc fragment function of the full-length antibody from which they are derived. Preferred functional fragments retain an antigen binding function of a corresponding full-length antibody. Certain preferred functional fragments retain the ability to inhibit one or more functions, such as a binding activity or a transport activity. In certain embodiments, the antibody may be used as a targeting agent to deliver a payload to a target cell.

In addition, a mixture of antibodies, termed herein as an "antibody preparation", can be used according to the methods of the present invention. Such antibody preparations include polyclonal and monoclonal mixtures of antibodies. Accordingly, an object of the present invention is to provide methods of treating a disease or disorder comprising administering an antibody preparation comprising conjugated biotin moieties, wherein said biotin moiety conjugated antibodies in said antibody preparation have increased serum half-life relative to antibodies of a preparation lacking the biotin moiety.

In one embodiment, the antibody preparation comprises polyclonal antibodies for use in intravenous immunoglobulin (IVIg) therapies. IVIg has been used since the early 1980s to treat immunological disorders. IVIg preparations usually contain more than 95 percent unmodified IgG, obtained from pooled human donors. Currently IVIg products are used to treat a wide range of disorders including immunodeficiencies, sepsis, neurological disorders, autoimmune and inflammatory diseases, and are also beneficial for transplantation reducing the allograft rejection.

In one embodiment, the antibody preparation is in addition sialylated at the N-linked glycan of the IgG Fc fragment, which can substantially enhance its anti-inflammatory effect by a mechanism distinct from FcRn binding (Kaneko et al., Science 313(5787), 670-673 (2006); Anthony et al., Science 320(5874), 373-376 (2008)). Biotinylation of IVIg acting to extend its serum half-life and concentrations maintained in circulation may thus further augment the efficacy of sialylated IgG and derivatives thereof.

In specific embodiments, the present invention relates to biotinylation of immunoglobulins, chimeric antibodies, humanized antibodies, or fully human antibodies for use in methods of treatment. For example, a humanized antibody can be an antibody derived from a non-human species, in which certain amino acids in the framework and constant domains of the heavy and light chains have been mutated so as to reduce of abolish an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293.

A humanized antibody may comprise portions of immunoglobulins of different origin. For example, at least one portion can be of human origin. For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Alternatively, a humanized antibody may be created in a transgenic or humanized animal expressing the human antibody genes (see Lonberg, N. "Transgenic Approaches to Human Monoclonal Antibodies." Handbook of Experimental Pharmacology 113 (1994): 49-101).

Another example of a humanized antibody of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). Chimeric or CDR-grafted single chain antibodies are also encompassed by the term "humanized antibody".

Methods of preparing immunoglobulins, immunizing with antigens, and polyclonal and monoclonal antibody production can be performed as described herein, or using other suitable techniques. A variety of methods have been described. See e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991; Rasmussen S K, Rasmussen L K, Weilguny D, Tolstrup A B. Biotechnol Lett. 2007 Feb. 20.) Generally, a hybridoma can be produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) can be isolated using selective culture conditions, and cloned by limiting dilution. Cells that produce antibodies with the desired specificity can be selected by a suitable assay (e.g., ELISA).

Antibodies can be purified from the plasma of human donors. This is the current approach for IVIg where immunoglobulins are isolated from normal plasma pooled from a large number of donors (see on the world wide web at fda.gov/cber/gdlns/igivimmuno.htm and Haeney Clin Exp Immunol. 1994 Jul.; 97(Suppl 1): 11-15.) At times IVIg is referred to herein as IGIV.

Other suitable methods for producing or isolating antibodies of the requisite specificity can be used, including, for example, methods which select recombinant antibodies from a library, or which rely upon immunization of transgenic animals (e.g., mice) capable of producing a full repertoire of human antibodies. See e.g., Jakobovits et al., Proc. Natl. Acad. Sci. USA, 90: 2551-2555 (1993); Jakobovits et al., Nature, 362: 255-258 (1993); Lonberg et al., U.S. Pat. No. 5,545,806; Surani et al., U.S. Pat. No. 5,545,807.

An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, as described below.

The term "chimeric antibody" refers to an antibody that contains one or more regions from one antibody and one or more regions from one or more other different antibodies. In one embodiment, one or more of the CDRs are derived from a specific human antibody. In a more preferred embodiment, all of the CDRs are derived from a human antibody. In another preferred embodiment, the CDRs from more than one human antibody are mixed and matched in a chimeric antibody. For instance, a chimeric antibody may comprise a CDR1 from the light chain of a first human antibody combined with CDR2 and CDR3 from the light chain of a second human antibody, and the CDRs from the heavy chain may be derived from a third antibody. Further, the framework regions may be derived from one of the same antibodies, from one or more different antibodies, such as a human antibody, or from a humanized antibody.

In certain embodiments, the antibody is linked to an additional functional moiety. Such linkage may be covalent or non-covalent. In one embodiment, the functional moiety may be therapeutic, e.g., a drug conjugate or toxin.

In certain embodiments, the antibody is in addition glycosylated or sialylated.

In certain embodiments, the antibody may be covalently linked to cytotoxic drugs, small molecules, enzymatic proteins, plant toxins, bacterial toxins, radioisotopes or radionuclides (Junutula et al., 2008; Polakis, 2005; Wu and Senter, 2005). Examples of cytotoxins are calicheamicin, duocarmycin, mertanisien, maytansinoids, auristatin, 131I, 90Y, 214Bi, *Pseudomonas* Exotoxin PE38, Diphtheria toxin, ricin, saporin, doxorubicin and RNase.

In certain further embodiments, the antibody is labeled to facilitate detection. As used herein, the terms "label" or "labeled" refers to incorporation of another molecule in the antibody. In one embodiment, the label is a detectable marker, e.g., incorporation of a radiolabeled amino acid. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, beta-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In certain embodiments, the antibodies are further attached to a label that can be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radio scintigraphy, nuclear magnetic resonance imaging, computed tomography, or positron emission tomography. Immunoscintigraphy using antibodies or other binding polypeptides may be used to detect and/or diagnose cancers and vasculature. For example, monoclonal antibodies labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, and most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

In other embodiments, the antibodies are manufactured in prokaryotic or eukaryotic cells capable of being transformed or transfected with exogenous DNA and grown in culture. Such prokaryotic cells are *Escherichia coli* or *Bacillus*. Such eukaryotic cells are mammalian or fungal cells, algae or plant cells. Such mammalian cells include Chinese hamster ovary (CHO), murine lymphoid cells (including NS0 and Sp2/0-Ag 14), hybridomas, the hamster line BHK21, the human PER.C6 cell line and the like. Fungal cells, including species of yeast (e.g., *Saccharomyces* spp., *Schizosaccharomyces* spp., *Pichia pastoris*), or filamentous fungi (e.g., *Aspergillus* spp., *Neurospora* spp.) may be used as host cells within the present invention. Algae or microalgae including *Anabaena cylindrica, Aphanizomenon flos-aquae, Chlamydomonas rheinhardii, Chlorella pyrenoidosa, Chlorella vulgaris, Dunaliella salina, Euglena gracilis, Porphyridium cruentum, Scenedesmus obliquus, Spirogyra* sp., *Arthrospira maxima, Spirulina platensis* and *Synechococcus* sp. may be used as host cells within the present invention. In certain embodiments, the antibodies are manufactured in transgenic animals (e.g. mouse, rat, goat, sheep, pig, rabbit, bovine, chicken etc.) or transgenic plants. Transgenic plants including species of tobacco (e.g. *Nicotiana tabacum*), potato, pea, alfalfa, tomato, barley, and Maize.

As used herein, the term "increase the half-life" or simply "increased half-life" indicates that the in vivo half-life of an antibody or Fc fusion polypeptide comprising a conjugated biotin is at least 10% higher than the in vivo half-life of a comparable, control antibody or Fc fusion polypeptide not comprising a biotin. It is preferred that the half-life of an antibody or Fc fusion polypeptide comprising a conjugated biotin is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more, than a control antibody or Fc fusion polypeptide not comprising a biotin. To avoid doubt, the FcRn humanized mouse model, described herein in the Examples, can be used to determine in vivo half-life of said antibodies or Fc fusion polypeptides described herein.

Fc Fusion Proteins

An object of the present invention is to provide methods of treating a disorder in a subject in need thereof, comprising administering to the subject an effective amount of an Fc fusion polypeptide conjugated to a biotin moiety. Accordingly, the Fc fusion polypeptide comprises a human Fc domain fused to a heterologous fusion partner polypeptide, wherein the human Fc domain comprises a conjugated biotin moiety. The conjugation of the Fc fragment can be achieved by using genetic engineering techniques or chemical coupling methods well established in the art.

The terms "Fc domain" or "Fc fragment", interchangeably used herein, encompass native and altered forms of polypeptides derived from the Fc region of an antibody, preferably a human antibody, that are bound by FcRn. The Fc domain normally has at least two heavy chain constant region domains (CH2 and CH3). To avoid confusion, the natural human Fc domain refers to the human Fc domain sequence encompassed by the teachings of Kabat, herein incorporated by reference Kabat Sequences of Proteins of Immunological Interest (National Institutes of Health, Bethesda, Md. (1987 and 1991)). Forms of such polypeptides containing the hinge region that promotes dimerization are also included. One suitable Fc fragment, described in PCT applications WO05047334A1 and in WO04074455A2, is a single chain polypeptide extending from the N-terminal hinge region to the native C-terminus. It may be desirable to use altered forms of Fc fragments having improved serum half-life, altered effector functions, altered spatial orientation, and the like. The alteration of the Fc fragment can be achieved using genetic engineering techniques known in the art.

Immunoglobulin heavy chain constant region domains include CH1, CH2, CH3, and CH4 of any class of immunoglobulin heavy chain including gamma, alpha, epsilon, mu, and delta classes. A particularly preferred immunoglobulin heavy chain constant region domain is human CH2 and CH3. DNA sequences encoding immunoglobulins may be cloned from a variety of genomic or cDNA libraries known in the art. The techniques for isolating such DNA sequences using probe-based methods are conventional techniques and are well known to those skilled in the art. Probes for isolating such DNA sequences may be based on published DNA sequences (see, for example, Hieter et al., Cell 22: 197-207, 1980). Alternatively, the polymerase chain reaction (PCR) method disclosed by Mullis et al. (U.S. Pat. No. 4,683,195) and Mullis (U.S. Pat. No. 4,683,202), incorporated herein by reference may be used. The choice of library and selection of probes for the isolation of such DNA sequences is within the level of one of ordinary skill in the art.

In one embodiment, a particular polypeptide is fused C-terminally to the N-terminus of the constant region of immunoglobulins in place of the variable region(s) thereof, however N-terminal fusions of the binding partner may also be constructed. Typically, such fusions retain at least the functionally active hinge, CH2 and CH3 domains of the constant region of an immunoglobulin heavy chain, herein referred to as the "CH2—CH3-hinge" region. Fusion polypeptides for use in the present invention are also made to the C-terminus of the Fc portion of a constant domain, or immediately N-terminal to the CH1 of the heavy chain or the corresponding region of the light chain. This can be accomplished by constructing the appropriate DNA sequence and expressing it in recombinant cell culture. Alternatively, there may be a spacer (also called linker) included between the Fc domain and the polypeptide. In addition, the Fc domain may be modified to introduce functional groups such as lysines or cysteines, to allow or improve the conjugation of the biotin. Such modifications can be introduced using genetic mutagenesis approaches known in the art.

Furthermore, the Fc domain may be synthesized according to known methods. For example, the Fc domain may be produced by recombinant DNA techniques or by enzymatic (e.g. papain cleavage) or chemical cleavage of intact antibodies. Host cells for use in preparing Fc domain fusion polypeptides include prokaryotic and eukaryotic cells capable of being transformed or transfected with exogenous DNA and grown in culture, such as *Escherichia coli*, cultured mammalian and fungal cells or plant cells. Mammalian cells include Chinese hamster ovary (CHO), the hamster line BHK21, the human PER.C6 cell line, COS, NIH 3T3, BHK, HEK, 293, L929, MEL, JEG-3, murine lymphoid cells (including NS0 and Sp2/0-Ag 14), hybridoma cells. Fungal cells, including species of yeast (e.g., *Saccharomyces* spp., *Schizosaccharomyces* spp., *Pichia pastoris*), or filamentous fungi (e.g., *Aspergillus* spp., *Neurospora* spp.) may be used as host cells within the present invention. Algae including *Anabaena cylindrica*, *Aphanizomenon flos-aquae*, *Chlamydomonas rheinhardii*, *Chlorella pyrenoidosa*, *Chlorella vulgaris*, *Dunaliella salina*, *Euglena gracilis*, *Porphyridium cruentum*, *Scenedesmus obliquus*, *Spirogyra* sp., *Arthrospira maxima*, *Spirulina platensis* and *Synechococcus* sp. In certain embodiments, the antibodies are manufactured in transgenic animals (e.g. goat) or transgenic plants. Transgenic plants including species of tobacco (e.g. *Nicotiana tabacum*), potato, pea, alfalfa, tomato, barley, Maize. Further transgenic animals may be used to produce the recombinant protein, for example transgenic mice, rats, chicken, goat, rabbit, pig, sheep or cow may be used.

Furthermore, the Fc domain may be in addition glycosylated or sialylated.

The polypeptide or protein fused to the biotinylated Fc domain can be a growth factor, a cytokine, an enzyme, a receptor domain, an antibody fragment (single chain (scFv), Fab fragment domain antibody), a camelid, a llama, an alternative binding protein, antibody substructure, minibody, adnectin, anticalin, affibody, affilin, knottin, glubody, C-type lectin-like domain protein, designed ankyrin-repeat proteins (DARPin), tetranectin, kunitz domain protein, maxybody, thioredoxin, cytochrome b562, zinc finger scaffold, *Staphylococcal* nuclease scaffold, fibronectin or fibronectin dimer, tenascin, N-cadherin, E-cadherin, ICAM, titin, GCSF-receptor, cytokine receptor, glycosidase inhibitor, antibiotic chromoprotein, myelin membrane adhesion molecule P0, CD8, CD4, CD2, class I MHC, T-cell antigen receptor, CD1, C2 and I-set domains of VCAM-1,1-set immunoglobulin domain of myosin-binding protein C, 1-set immunoglobulin domain of myosin-binding protein H, I-set immunoglobulin domain of telokin, NCAM, twitchin, neuroglian, growth hormone receptor, erythropoietin receptor, prolactin receptor, interferon-gamma receptor, β-galactosidase/glucuronidase, β-glucuronidase, transglutaminase, T-cell antigen receptor, superoxide dismutase, tissue factor domain, cytochrome F, green fluorescent protein, GroEL, thaumatin, a matrix protein or the like.

Non-limiting examples of Fc fusion polypeptides are the fusion of IL-1 to the Fc fragment (IL-1 trap), VEGF to the Fc fragment (VEGF trap), DNase I-Fc fusion, E-cadherin Fc fusion, PTH-Fc Fusion, single chain antibody fusion, domain antibody fusion and etanercept (human p75 TNF-alpha receptor Fc fusion). The biotinylated fusion polypeptides of the present invention are useful in a variety of applications, including research and therapeutic applications.

Biotin Moieties and Biotinylation

In certain aspects, the present invention relates to methods of treatment involving the administration of antibodies and Fc fusion polypeptides with biotin moieties. Biotin is also known as hexahydro-2-oxo-1H-thieno[3,4-d]imidazole-4-pentanoic acid, vitamin B7, vitamin H, Coenzyme R or Biopeiderm. Biotin was first isolated in 1936 and is an essential nutrient factor in mammals. Its chemical formula is $C_{10}H_{16}N_2O_3S$. It is water soluble, hydrophobic and small, with a molecular weight of 244.31. Biotin is a bicyclic molecule composed of an ureido ring fused with a tetrahydrothiophene (or thiophane) ring. Although biotin in doses below 5 mg daily is not toxic, when taken above 5 mg daily for one month or longer dihydrotestrone-like symptoms may develop (Andersen, 2001). Biotin functions as a cofactor in carboxylation, decarboxylation, and transcarboxylation reactions related to biochemical processes, such as glucogenesis and fatty acid synthesis.

In the laboratory biotin can be covalently linked to both proteins and nucleic acids, and is widely used as a label in many molecular biology and biochemistry technologies, especially together with avidin or streptavidin as a detection molecule (ELISA, ELISPOT). For example, owing to the high affinity of biotin to avidin or streptavidin, biotin is commonly used as a tag for protein purification and diagnostics. Biotin has also been used as a coupling molecule for the creation of bispecific antibodies or tetrabodies and prodrug approaches.

In certain embodiments of the present invention, biotin derivatives or analogs can be applied. Thus, as used herein, the term "biotin moiety" includes biotin and its derivatives and analogs, such as 2-iminobiotin. Other biotin derivatives or analogs that can be applied to the objects of the present invention include, but are not limited to, biocytin (-biotinoyl-L-lysine), biotin ethylenediamine, biotin cadaverine, biotin-X cadaverine, DSB-X desthiobiocytin (-desthiobiotinoyl-L-lysine) and DSB-X biotin ethylenediamine and chloroacetylated biotin derivative (CABI), as well as other biotin analogs commonly known in the art. A "biotin moiety", as the term is used herein, will increase the serum half-life of an antibody or Fc-domain containing fusion polypeptide.

In certain embodiments biotinylation can be achieved by a chemical reaction in vitro or in an in vivo system, e.g. utilizing the *E. coli* biotin holoenzyme synthetase and is well established in the art (Bayer and Wilchek, 1990; Haugland and You, 1995, 1998; Yeo et al., 2004). In other embodiments, through chemical conjugation, biotin can be coupled to primary and epsilon amines of lysine either directly or via a spacer to the Fc polypeptide. Here, the term "Fc polypeptide" includes Fc fragments, antibodies, antibody fragments containing an Fc fragment, as well as Fc fusion polypeptides, or the like. The amines of the Fc polypeptide that can be easily targeted are most commonly lysine residues, using for example the N-hydroxysuccinimide (NHS) ester chemistry (NHS CAS Number 6066-82-6). An exemplary method is to label the epsilon-amino groups of lysine residues with a succinimidyl ester of biotin (Ugarova et al., 1979). Any primary amine or epsilon amine reacts with NHS esters and can therefore be targeted for crosslinking using the N-hydroxysuccinimide (NHS) ester chemistry.

In preferred embodiments of the present invention, the Fc fragment of the antibody or Fc fusion polypeptide may be mutagenized such that only one, two or three lysine residues are available for crosslinking to a biotin moiety. For example, lysines not to be used for biotin conjugation can be mutagenized to alanine. In a preferred embodiment, new lysine residues can be introduced to allow additional and/or site-specific biotinylation.

Alternatively, in other embodiments, cysteines on the Fc fragment of the antibodies or Fc fusion polypeptides can be biotinylated. Specific reactive cysteine residues can be genetically engineered into the Fc fragment using methods known in the art. For example, a solvent exposed cysteinyl residue can be engineered onto IgG, such that it creates a solvent exposed cysteine, thus making it available for conjugation, for example using Iodoacetyl-Biotin, which reacts with the sulfhydryl group (—SH) of the cysteine and forms a stabile thioether linkage. The use of iodoacetyl compounds for linking toxins or labels to antibodies or proteins has been demonstrated. Examples include the attachment of PEG to proteins, e.g., PEGylated colony stimulating factor (pegfilgrastim), PEGylated interferon alpha (pegasys). Biotin can be conjugated to the thiol group of the cysteine using standard coupling chemistry (Wong, 1991) or the THIOMAB technology as described in (Junutula et al., 2008). In one embodiment, lysine residues can be replaced by reactive cysteine residues. As but a few examples, one or more cysteines can replace the biotin-targeted lysine residue in the Fc domain sequence of SEQ ID NO:1, SEQ ID NO:2, and/or SEQ ID NO:3. Thus, example sequences can include:

| | |
|---|---|
| SEQ ID NO 4: | FNWYVDGVEVHNACTKPR |
| SEQ ID NO 5: | FNWYVDGVEVHNAKTCPR |
| SEQ ID NO 6: | FNWYVDGVEVHNACTCPR |
| SEQ ID NO 7: | FCWYVDGVEVHNAKTKPR |
| SEQ ID NO 8: | FKWYVDGVEVHNACTKPR |
| SEQ ID NO 9: | FKWYVDGVEVHNAKTCPR |
| SEQ ID NO 10: | FCWYVDGVEVHNACTKPR |
| SEQ ID NO 11: | FCWYVDGVEVHNAKTCPR |
| SEQ ID NO 12: | FKWYVDGVEVHNACTCPR |
| SEQ ID NO 13: | FCWYVDGVEVHNACTCPR |
| SEQ ID NO 14: | VSNCALPAPIEK |
| SEQ ID NO 15: | VSNKALPAPIEC |
| SEQ ID NO 16: | VSNCALPAPIEC |

In alternative embodiments, other reactive amino acids may be targeted for conjugation: gamma and beta-carboxyl groups of glutamic and aspartic acids, imidazolyl group of histidine, thioether moiety of methionine, indolyl group of tryptophan, and phenolic hydroxyl group of tyrosine (Wong, 1991). For example, thiol or aldehyde groups of the protein may be targets. Additionally, sulfhydryl groups of the Fc fragment can be biotinylated using biotin iodoacetamide or maleimide. Furthermore, carboxyl groups of aspartic- and glutamic acid residues of the Fc fragment can be biotinylated, for example, with Biotin-PEO-Amine, Biotin-PEO-LC-Amine or 5-(biotinamido)-pentylamine.

In another embodiment, other coupling methods may be applied, including a synthetic method, for example the "click" chemistry (Lutz and Boerner, 2008; Moses and Moorhouse, 2007). Carbohydrate groups of the Fc fragment may also be biotinylated, in another embodiment, for example, with biotin hydrazide (Biotin-LC Hydrazide, Pierce catalog No. 21340.

In a preferred embodiment, one or more biotin moieties may be conjugated to a target protein (e.g., an antibody or an Fc fusion polypeptide). In one embodiment, a human IgG antibody has an average of 2.4 biotin moieties/IgG molecule to achieve an increase in plasma half-life. In other embodiments, a human IgG antibody has an average of 7.2 biotin moieties/IgG molecule. For human IgG molecules the addition of at least 2 or more (e.g., between 2-10) biotin molecules per IgG increases the half-life correlating to the number of biotin moieties.

In a preferred embodiment, one or more biotin moieties may be conjugated to the Fc fragment, to the CH2—CH3-hinge domain of the Fc fragment, or to the hinge region at the CH2—CH3 domain interface of the Fc fragment. The naturally occurring Fc domain is a dimer of the hinge region and the second and third constant regions (CH2 and CH3 domain). Biotinylation of each monomer at a single site can be sufficient to increase the half-life of the antibody or Fc fusion polypeptide, such that at least one biotin moiety per Fc monomer is sufficient to increase half-life. Thus, in one embodiment, an Fc domain monomer, i.e., a CH2—CH3-hinge region monomer, comprising a single conjugated biotin moiety can have increased half-life, relative to an Fc domain monomer not comprising the biotin moiety.

In another embodiment, one or more biotin moieties may be conjugated to the following lysine residues of the human IGHG1 Fc fragment K246, K274, K288, K317, K320, K326, K334, K340, K360, K370, K392, K409, K414 and K439 (UniProtKB/Swiss-Prot P01857; SEQ ID NO: 17) or corresponding lysine residues for other Fc fragments. In a preferred embodiment, the preferred lysine residues are selected from the group consisting of K288, K290, K317, K326, K340, K360, and K439.

In another preferred embodiment, the lysine residues K288 and/or K326 of the human IGHG1 Fc fragment or the corresponding lysine residues for other Fc fragments are biotinylated.

In another embodiment, the lysine residue to undergo conjugation to a biotin moiety in an Fc fragment is identified using alignment tools and subsequent alignment of the sequence to the consensus peptide of SEQ ID NO: 1 or SEQ ID NO: 2 or SEQ ID NO: 3

In another embodiment, the corresponding lysine residues are identified using techniques known in the art, for example sequence alignment and 3D protein modeling tools.

In other embodiments of the present invention, a mixture of human target proteins (e.g., an antibody or an Fc fusion polypeptide) is biotinylated. In one embodiment, a human antibody IgG subtype is biotinylated. In certain embodiments, a spacer is used for coupling of biotin to the target protein. The term "spacer" is used here for chemical group or a short peptide that is between the target protein and the biotin molecule. Such spacers are also referred to herein as a cross-linker or linker. In the case of a peptide spacer, this peptide may have a length from 1 to 20 amino acids comprising a higher number of alanine and glycines. The spacer may also contain a specific number of glycines and/or prolines to give flexibility and/or rigidity. The optimal spacer may be determined using computational and protein design tools to select favorable spacers.

In certain embodiments of the invention, a spacer is a chemical molecule, such as N-hydroxysuccinimide (NHS), NHS-LC, NHS-LC-LC, N-Hydroxysulfosuccinimide (Sulfo-NHS) esters, N-succinimidyl-3-(2-pyridyldithio)propionate (SPDP), Succinimidyl 6-(3-[2-pyridyldithio]-propionamido)hexanoate (LC-SPDP), Biotin-PEO-Amine, Biotin-PEO-LC-Amine or 5-(biotinamido)-pentylamine. A wide variety of coupling reagents are commercially available (e.g. Pierce). In certain embodiments, the spacer may be Succinimidyl-6-(biotinamido)hexanoate (NHS-LC biotin), with a size of 22.4 Å, or N-Hydroxysuccinimidobiotin (NHS-biotin), with a size of 13.4 Å.

In other embodiments, a biotinylated antibody or Fc fusion polypeptide may optionally comprise one or more additional modifications for further increased persistence in vivo. Examples of such additional modifications include, but are not limited to, PEGylation, glycosylation, sialylation, albumin conjugation, and mutagenesis within the target protein, and mutagenesis of the Fc domain. In the case of amino acid mutagenesis in the Fc domain, it is known that certain modifications can increase binding to the FcRn receptor and extend the half life. Examples for such substitutions are N434A and T307/E380/N434 (Petkova et al., 2006c) and others described in (Dall'Acqua et al., 2006; Hinton et al., 2007; Hinton et al., 2006).

```
SEQ ID NO: 17:
human IGHG1 (UniProtKB/Swiss-Prot P01857)
ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFF
LYSKLTVDKSRWQQGNVFSCSVMHEALHNHYTQKSLSLSPGK

SEQ ID NO: 1:
FNWYVDGVEVHNA̲K̲T̲K̲PR

SEQ ID NO: 2:
FK̲WYVDGVEVHNA̲K̲T̲K̲PR

SEQ ID NO: 3:
VSNK̲ALPAPIEK̲
```

Therapeutic Applications

In certain embodiments, the present invention provides methods and compositions for treating various disorders. The methods involve administering to the individual a therapeutically effective amount of one or more biotinylated antibodies or biotinylated Fc fusion proteins as described above. These methods are particularly aimed at therapeutic and prophylactic treatments of animals, and more particularly, humans.

Antibody therapeutics have been proven to be effective for a wide number of diseases (Carter, 2006). The majority of antibodies developed to date are to treat cancer: Herceptin for the treatment of breast cancer, Erbitux for colorectal cancer and head and neck cancer, Mylotarg for acute myeloid leukemia, Rituxan, Zevalin and Bexxar for Non-Hodgkin lymphoma, Campath for B-cell chronic lymphocytic leukemia and Avastin for metastatic colorectal cancer, Non-Small Cell lung cancer and metastatic breast cancer. Another group of antibodies is used to prevent acute kidney transplant rejection (for example Simulect and Zenapax). Others diseases being treated with antibodies are inflammatory diseases, e.g. Remicade and Humira being approved for the treatment of Crohn's disease, psoriatic arthritis, rheumatoid arthritis and ankylosing spondylitis and Raptiva for the treatment of psoriasis.

Other indications are asthma (Xolair), multiple sclerosis (Tysabri), cardiovascular (ReoPro for the prevention of clots), infectious diseases (Synagis as prophylactic for prevention of RSV infection in children) and opthalmology, with Lucentis being approved to treat age-related macular degeneration (AMD). Antibodies are currently being evaluated for the treatment of amyotrophic lateral sclerosis, polyneuropathy, neurodegenerative diseases, infectious diseases and other disorders.

As described herein, cancer, neurodegenerative diseases, immunodeficiencies, cardiovascular diseases, inflammatory diseases, chronic diseases, eye disorders, transplantation, prenatal disorders, obesity, metabolic disorders, neurodegenerative diseases, infectious diseases and autoimmune diseases suitable for treatment by the subject biotinylated antibodies or Fc fusion polypeptides include, but are not limited to, breast cancer, head and neck cancer, colorectal cancer, colon cancer, lung cancer, prostate cancer, brain tumors, glioma, neuroblastoma, ovarian cancer, cervical cancer, melanoma, sarcoma, neoplasia, hepatocellular cancer, pancreatic cancer, renal cell cancer, bladder cancer, thyroid cancer, lymphoma, Non-Hodgkin Lymphoma, leukemia, hematopoietic tumors, oral cancer, esophageal cancer, inflammatory bowel disease, Crohn's disease, psoriatic arthritis, osteoarthritis, asthma, ankylosing spondylitis, psoriasis, age-related macular degeneration, retinopathy, uveitis, hepatitis, transplant rejection systemic lupus erythematosus, insulin resistant diabetes, lysosomal storage disease, myasthenia gravis, polyarteritis, autoimmune thrombocytopenic purpura, cutaneous vasculitis, bullous pemphigoid, pemphigus vulgaris, pemphigus foliaceus, Goodpasture's syndrome, rheumatoid arthritis, Kawasaki's disease, Sjogren's syndrome, osteoporosis, atherosclerosis, coronary heart disease, muscular dystrophy, amyotrophic lateral sclerosis, multiple sclerosis, stroke, Alzheimer's and Parkinson disease.

In certain embodiments of such methods, one or more biotinylated antibodies or biotinylated Fc fusion polypeptides can be administered, together (simultaneously) or at different times (sequentially). In other embodiments, the biotinylated antibodies or biotinylated Fc fusion polypeptides of the invention can be administered alone. Alternatively, they may be used in combination with an immunostimulatory agent, an immunomodulator, or a combination thereof. A wide array of conventional compounds has been shown to have immunomodulating activities, including but not limited to, alpha-interferon, gamma-interferon, tumor necrosis factor-alpha, or a combination thereof. The present invention recognizes the effectiveness of conventional therapies for autoimmune diseases, which can be enhanced through the use of one or more biotinylated antibodies or biotinylated Fc fusion polypeptides of the invention. Alternatively, they may be used in combination with chemotherapy or radiation therapy. Alternatively, they may be used together with chemotherapeutic such as alkylating agents (e.g. cisplatin, carboplatin, oxaliplatin, mechlorethamine, cyclophosphamide and chlorambucil), antimetabolites, anthracyclines, plant alkaloids (such as etoposide, teniposide, Paclitaxel and Docetaxel), topoisomerase inhibitors (such as irinotecan, topotecan, amsacrine, etoposide, etoposide phosphate, and teniposide), tyrosine kinase inhibitors (such as imatinib mesylate, dasatinib, lapatinib ditosylate, sorafenib, lestaurtinib, sunitinib maleate) and the like.

In certain embodiments of the invention, a preparation of biotinylated polyclonal antibodies can be administered as polyclonal therapies, which are effective for use in treatment of infectious diseases, cancer, inflammatory diseases, neurological disorders, autoimmune diseases, and immunodeficiencies. One such polyclonal therapy is known as IVIg (intravenous administration of heterologous immune globulin), which is also referred to as IgIV. IVIg is an invaluable FDA-approved palliative therapy for primary immune deficiencies, such as hypogammaglobulinemia, allogeneic bone marrow transplantation, chronic lymphocytic leukemia, pediatric HIV, idiopathic thrombocytopenic purpura (ITP), Kawasakis's disease and kidney transplants. Off label uses of IVIg include treatments for a wide array of syndromes, including multiple sclerosis, Guillain-Barré syndrome, lupus erythematosus, myasthenia gravis, pemphigus, spontaneous abortion, and severe sepsis (on the world wide web at en.wikipedia.org/wiki/Intravenous immunoglobulin).

There is evidence that IVIg therapy is beneficial for certain cancers, e.g. prostate cancer, melanoma, colon cancer. IVIg can be combined with other therapies, for example the combination of IVIg with Rituximab improves the chances successful kidney transplantations (Vo et al 2008, N Engl J Med. 2008 Jul 17;359(3):242-51).

In further embodiments, the biotinylated antibodies or biotinylated Fc fusion polypeptides of the present invention can be combined with a known therapy for autoimmune diseases. Examples of such known therapies for autoimmune diseases include, but are not limited to, therapies with nonsteroidal anti-inflammatory drugs (NSAID) or corticosteroids. Other examples of therapies for autoimmune diseases include periodic administration of patients with high doses of antibodies.

In certain embodiments of the present invention, a preparation of biotinylated antibodies, either monoclonal or polyclonal, can be administered for passive immunization. Examples for the use of the preparation of biotinylated antibodies in passive immunization include, but are not limited to, exposure to or infection with viruses, such as Hepatitis A virus, Hepatitis B virus, Variola virus, Rabies virus, Ebola virus, herpes simplex virus, varicella zoster virus, Epstein-Barr virus, tick-borne encephalitis virus, or a cytomegalovirus; exposure to a toxin, such as botulism toxin or snake venom toxin; exposure to or infection with a bacterial pathogen, such as *Bacillus anthracis*; and in immunosuppressive diseases.

Accordingly, the present invention provides methods for the delivery of a therapeutic antibody or fusion polypeptide across an epithelial layer, the method comprising administering to a subject in need thereof, an antibody or fusion polypeptide comprising an Fc domain, wherein the Fc domain comprises conjugated biotin, and wherein the biotinylated antibody or fusion polypeptide is delivered across the epithelial barrier with increased effectiveness relative to an antibody or fusion polypeptide lacking biotinylation of the Fc domain In certain specific embodiments, the biotinylated antibodies and Fc fusion polypeptides of the present invention more efficiently traverse mucosal epithelial layers, such as the respiratory and intestinal epithelial layers (Dickinson et al., 1999; Kim et al., 2004; Yoshida et al., 2004). In another embodiment, the biotinylated antibodies and Fc fusion polypeptides more efficiently traverse the corneal or olfactory epithelial layers. In certain embodiments, the present invention provides methods of treating disorders by administering biotinylated IgG antibodies or Fc fusion polypeptides that increase the acid pH-dependent but not the neutral pH-dependent binding avidity to human FcRn in vitro.

In another specific embodiment, the epithelial layer is an endothelial layer. In a more specific embodiment, the endothelial layer is a blood vessel or lymphatic vessel endothelial layer. In such embodiments, the invention provides methods for enhancing the FcRn-mediated transport across endothelial layers, such as, in a non-limiting example, from the bloodstream to extravascular sites, thus increasing their bioavailability in extravascular tissues, for use in the treatment of solid tumors.

As used herein, the term "epithelial cells" refers to cells that form the layer of cells lining the cavities and surfaces of structures throughout the body, forming the "epithelium" or "epithelial layer". Hence, the "epithelial layer", as referred to herein, comprises the cells that line both the outside (skin) and the inside cavities and lumen of bodies. The epithelial layer can further be sub-divided, according to shape and stratification of the epithelial cells, into squamous, columnar, cuboidal, stratified, simple, and pseudostratified epithelial layers. The epithelial layer is often defined by the expression of the adhesion molecule e-cadherin, as opposed to n-cadherin, which is used by cells of the connective tissue. Epithelial layers form the insides of the respiratory system, the gastrointestinal tract, the reproductive and urinary tracts, and constitute the exocrine and endocrine glands. In a non-limiting example, the outer surface of the cornea is covered with fast-growing, easily-regenerated epithelial cells.

An "endothelial layer", as the term is used herein, refers to a specialized form of epithelium comprising the inner lining of blood vessels, the heart, and lymphatic vessels, composed primarily of simple, squamous epithelial cells.

Accordingly, in one embodiment, a method is provided for the delivery of a therapeutic antibody or fusion polypeptide across a fetomaternal organ, the method comprising administering to a subject in need thereof, an antibody or fusion polypeptide comprising an Fc domain, wherein the Fc domain comprises conjugated biotin, and wherein the biotinylated antibody or fusion polypeptide is delivered across the maternal-fetal interface with increased effectiveness relative to an antibody or fusion polypeptide lacking biotinylation of the Fc domain. In a specific embodiment, the fetomaternal organ is the placenta. In such embodiments, the biotinylated antibodies or biotinylated Fc fusion polypeptides of the invention can be used for prenatal therapy. Non-limiting examples for uses of the biotinylated antibodies or Fc fusion polypeptides in prenatal therapy include lysosomal storage diseases, metabolic diseases, and infectious diseases (Grubb et al., 2008).

The "placenta", as the term is used herein, is an ephemeral organ present in placental vertebrates, such as eutherial mammals and sharks during gestation. The placenta develops from the same sperm and egg cells that form the fetus, and functions as a feto-maternal organ with two components, the fetal part (Chorion frondosum), and the maternal part (Decidua basalis).

Depending on the nature of the combinatorial therapy, administration of the biotinylated antibodies or biotinylated Fc fusion polypeptides of the invention may be continued while the other therapy is being administered and/or thereafter. Administration may be made in a single dose, or in multiple doses. In some instances, administration is commenced at least several days prior to the conventional therapy, while in other instances, administration is begun either immediately before or at the time of the administration of the conventional therapy. In certain specific embodiments, the therapeutic biotinylated agent is administered by subcutaneous, intravenous, intranasal, parenteral, transdermal, intratracheal, intravenous, intramuscular, intracranial, intrathecal or intravitreal injection; by oral administration, eye drops, pessary or inhalation.

Pharmaceutical Compositions and Modes of Administration

An object of the present invention, in part, is to provide improved therapeutic regimens, wherein administration of biotinylated antibodies and Fc fusion polypeptides, allows for less frequent dosage administrations and reduced effective doses, relative to antibodies and Fc fusion polypeptides not comprising a biotin moiety. In certain embodiments, the subject biotinylated antibodies or biotinylated Fc fusion polypeptides of the present invention are formulated with a pharmaceutically acceptable carrier. The biotinylated antibodies or biotinylated Fc fusion polypeptides can be administered alone or as a component of a pharmaceutical formulation (composition). They may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The subject formulations of the present invention include those suitable for oral, dietary, topical, parenteral (e.g., intravenous, intraarterial, intramuscular, subcutaneous injection), inhalation (e.g., intrabronchial, intranasal, or oral inhalation; intranasal drops), rectal, and/or intravaginal administration. Other suitable methods of administration can also include rechargeable or biodegradable devices and slow release polymeric devices. The pharmaceutical compositions of this invention can also be administered as part of a combinatorial therapy with other agents (either in the same formulation or in a separate formulation).

The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of immune-modulating agent and a carrier and, optionally, one or more accessory ingredients. In general, the formulations can be prepared with a liquid carrier, or a solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), and/or as mouth washes and the like, each containing a predetermined amount of one or more subject antibodies as an active ingredient.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Methods of the invention can be administered topically, for example, to the skin. The topical formulations may further include one or more of the wide variety of agents known to be effective as skin or stratum corneum penetration enhancers. Examples of these include 2-pyrrolidone, N-methyl-2-pyrrolidone, dimethylacetamide, dimethylformamide, propylene glycol, methyl or isopropyl alcohol, dimethyl sulfoxide, and azone.

Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject antibodies may be mixed under sterile conditions with a pharmaceutically acceptable carrier, and with any preservatives, buffers, or propellants which may be required. The ointments, pastes, creams and gels may contain, in addition to a biotinylated antibody or Fc fusion polypeptide, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Pharmaceutical compositions suitable for parenteral administration may comprise one or more biotinylated antibodies or biotinylated Fc fusion proteins in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

In addition, prolonged absorption of the injectable pharmaceutical form may be brought about by the inclusion of agents which delay absorption, such as aluminum monostearate and gelatin. Injectable depot forms are made by forming microencapsule matrices of one or more antibodies in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides), collagen, hydrogel, chitosan and alginate. Depot injectable formulations are also prepared by entrapping the drug in liposomes, polymeric nanoparticles or microemulsions which are compatible with body tissue.

In certain embodiments, the pharmaceutical composition is administered by subcutaneous, intravenous, intranasal, parenteral, transdermal, intracheal, intravenous, intramuscular, intracranial, intrathecal or intravitreal injection; by oral administration, eye drops, pessary; inhalation or implantation.

EXEMPLIFICATION

The invention now being generally described will be more readily understood by reference to the following examples, which are included merely for purposes of illustration of certain aspects and embodiments of the present invention, and are not intended to limit the invention.

Example 1

Biotinylation of Human Immunoglobulin G

Purified human immunoglobulin G (hIgG) (Gammagard, Baxter) was conjugated with biotin by first diluting the hIgG stock in 50 mM sodium phosphate buffer, pH 7.2 with the same buffer to 2.2 mg/ml, or $1.37 \times 10^{-5}$ M. N-hydroxysuccinimidobiotin (EZ-Link™ NHS-biotin, Pierce cat. #20217) was allowed to come to room temperature, then a $3.42 \times 10^{-3}$ M solution of NHS-biotin in DMSO (10× strength) was produced. One volume of $3.42 \times 10^{-3}$ M (10×) NHS-biotin was added to 9 volumes of $1.37 \times 10^{-5}$ M hIgG to achieve a 25-fold excess molar concentration of NHS-biotin. The reaction was performed for 30 minutes at room temperature, then 1 volume of 1 M glycine, pH 7.2 was added to stop the reaction. The reactants were twice dialyzed in 5 liters of 50 mM sodium phosphate buffer, pH 7.2 at 4° C. The hIgG-biotin solution was sterile filtered using a 0.45 µm pore syringe filter and stored at 4° C. To determine the biotin:hIgG ratio the EZ Biotin Quantitation Kit (Pierce cat. #28005) in the microplate format method was used, assaying all samples in triplicate. 100 µl of pure water was added to each No-Weigh™ HABA/Avidin Premix. 160 µl 50 mM sodium phosphate buffer, pH 7.2 was added into wells of a microplate. 20 µl of the HABA/Avidin Premix solution was added to the PBS in the wells. The average $A_{500\ nm}$ HABA/avidin equaled 0.542. 20 µl of hIgG-biotin, or biotinylated standard included in the kit was added. The average $A_{500\ nm}$ HABA/avidin/biotin equaled 0.501. The average $A_{280\ nm}$ of hIgG-biotin was determined to be 2.044 and divided by the extinction coefficient 1.4 to determine the protein concentration as 1.46 mg/ml. According to the Beer Lambert Law: $A_\lambda = \varepsilon_\lambda bC$, where A is the absorbance of a sample at a particular wavelength ($\lambda$). $\varepsilon$ is the extinction coefficient at the wavelength $\lambda$. For HABA/avidin at 500 nm, pH 7.0, the extinction coefficient equals 34,000 ml/(M$^{-1}$ cm$^{-1}$). b is the light's path length through the sample expressed in cm. C is the concentration of the sample expressed in mmol/ml. Applied this equation to the values obtained above, $$\frac{\text{mmol biotin}}{\text{mmol } hIgG} = \frac{(\Delta A_{500nm}/(34{,}000 \text{ ml}/(\text{M}^{-1}\text{cm}^{-1}) \times b))(20)}{(A_{280nm}/1.4)/146{,}000 \text{ g/mol}}$$

$$= \frac{(0.041/(34{,}000 \times 0.5)) \times 20}{(2.044/1.4)/146{,}000}$$

$$= 4.8$$

the biotin:hIgG ratio, where $\Delta A_{500\ nm}$ equals $A_{500}$ HABA/avidin minus $A_{500}$ HABA/avidin/biotin, 20 was a correction factor for the combination 2-fold predilution and 10-fold dilution of the hIgG-biotin in the hIgG-biotin/HABA/avidin mixture, and 146,000 g/mol is the molecular weight of hIgG.

Example 2

Determination of hIgG-biotin Half Life In Vivo

To determine the effect of biotinylation on the in vivo half life of hIgG, C57BL/6 mFcRn−/− hFcRn +/Tg Line 276 mice (3-5 mice/group) were given intraperitoneal injections of 100 µg of hIgG with, or without, biotin conjugation at day-3. C57BL/6 mFcRn−/− hFcRn +/Tg Line 276 mice do lack the mouse FcRn gene and do express the human FcRn. For a more detailed description of the mouse model, see (Petkova et al., 2006a). Plasma was obtained 3 days after tracer injection (to avoid the alpha phase of hIgG degradation), at day 0, 7, 14, 21, and 28, by collecting either 25 µl, or 75 µl of blood from the retro-orbital sinus into capillary tubes and transferring to 1.5 ml microcentrifuge tubes containing 2 µl of PBS with 10,000 U/ml heparin. Tubes were centrifuged at 10,000 rpm for 5 minutes at 4° C. in an Eppendorf 5417R centrifuge (New York). Plasma samples were transferred to 96 well round bottom polypropylene storage plates (Corning cat. #3365), plug seal covered with Microplate Storage MattII covers (Corning cat. #3092) and stored at −70° C. The storage plate was sandwiched between freezer packs to minimize volume loss to by evaporation.

Quantitation of hIgG by ELISA hIgG specific ELISA of plasma samples was performed using 96 well high binding ELISA plates (Greiner cat#655061) coated with mouse anti-human IgG-Fc (Southern Biotech cat. #9040-01) diluted to 0.5 µg/100 µl/well in Dulbecco's phosphate buffered saline, pH 7.2 (DPBS, Hyclone cat. # SH30013) overnight at 4° C. Plates were hand washed using a manifold with 96 nozzles connected to a 30 ml syringe (Bel Art Vaccupette/96) 2 times 300 µl per well using DPBS with 0.05% Tween 20 and 0.05% sodium azide (ELISA Wash). Wash was removed by flicking plates into a sink and blotting the plates on paper towels. Plates were blocked with 300 µl/well of ELISA Block (ELISA Wash with 1% bovine serum albumin (BSA, Fitzgerald cat. #30-AB75)) for a minimum of 1 hour at room temperature. Plasma samples were diluted 1/200 with diluent (same as ELISA Block). HIgG and hIgG-biotin were diluted 2-fold from 1000 ng/ml down to 1 ng/ml to act as standards. Block was removed by flicking and blotting as before. 100 µl of diluted standards and plasma as well as diluent only (to act as blanks) were transferred into the coated and blocked ELISA plates. Plates were incubated at 37° C. for 1 hour, then washed as before 3 times 300 μl/well. Added 100 μl/well of mouse anti-human kappa-AP (Southern Biotech cat. #9220-04) diluted 1/1000 in diluent and incubated at 37° C. for 1 hour, then washed as before 3 times 300 μl/well. Added 100 μl/well of 1 mg/ml p-nitrophenyl phosphate (Sigma Cat. # N2765) in Substrate Buffer (20 mM sodium bicarbonate, 24 mM sodium carbonate, 7 mM magnesium chloride hexahydrate, pH 8.6). Read $A_{405\,nm}$ at 30 minutes, or when the maximum optical density exceeded 1. Data is plotted as the percent tracer remaining compared to the day 0 plasma tracer concentration. Half-life was calculated using the formula:

$$t_{1/2} = \frac{\log 0.5}{\log A_e/A_o} \times t$$

where $t_{1/2}$ is the half life of the tracer, $A_e$ is the amount of tracer left, $A_o$ is the original amount of tracer at day 0, and t is the elapsed time.

This data indicates that when biotin is conjugated to the available lysine residues on hIgG and injected into the peritoneal cavity of C57BL/6 mFcRn−/− hFcRn +/Tg Line 276 mice, hIgG-biotin has a longer half-life compared to hIgG.

Analysis by a Second ELISA Assay

In addition to the mouse anti-human kappa-AP detection reagent described above, Streptavidin-horse radish peroxidase (SAv-HRP, Southern Biotech cat. #7100-05) was used as a second detection reagent. First, a hIgG ELISA was performed as described above, except azide-free buffers were used to preserve the SAv-HRP activity. After the alkaline phosphatase (AP) activity was measured, the plates were washed as described above 1 times 300 μl/well. Added 100 μl/well SAv-HRP diluted 1/1000 in azide-free diluent right into the very same washed plates that had just had their mouse anti-kappa-AP activity measured, and incubated 1 hour at 37° C. Plates were washed as described above 3 times 300 μl/well. Added 100 μl/well 3,3',5,5' tetramethylbenzidine (TMB, Pierce cat #34028) as a horseradish peroxidase (HRP) substrate. After 30 minutes of color development, added 50 μl/well of 2 M sulfuric acid to stop the reaction, and measured the $A_{450\,nm}$.

Figure 2:
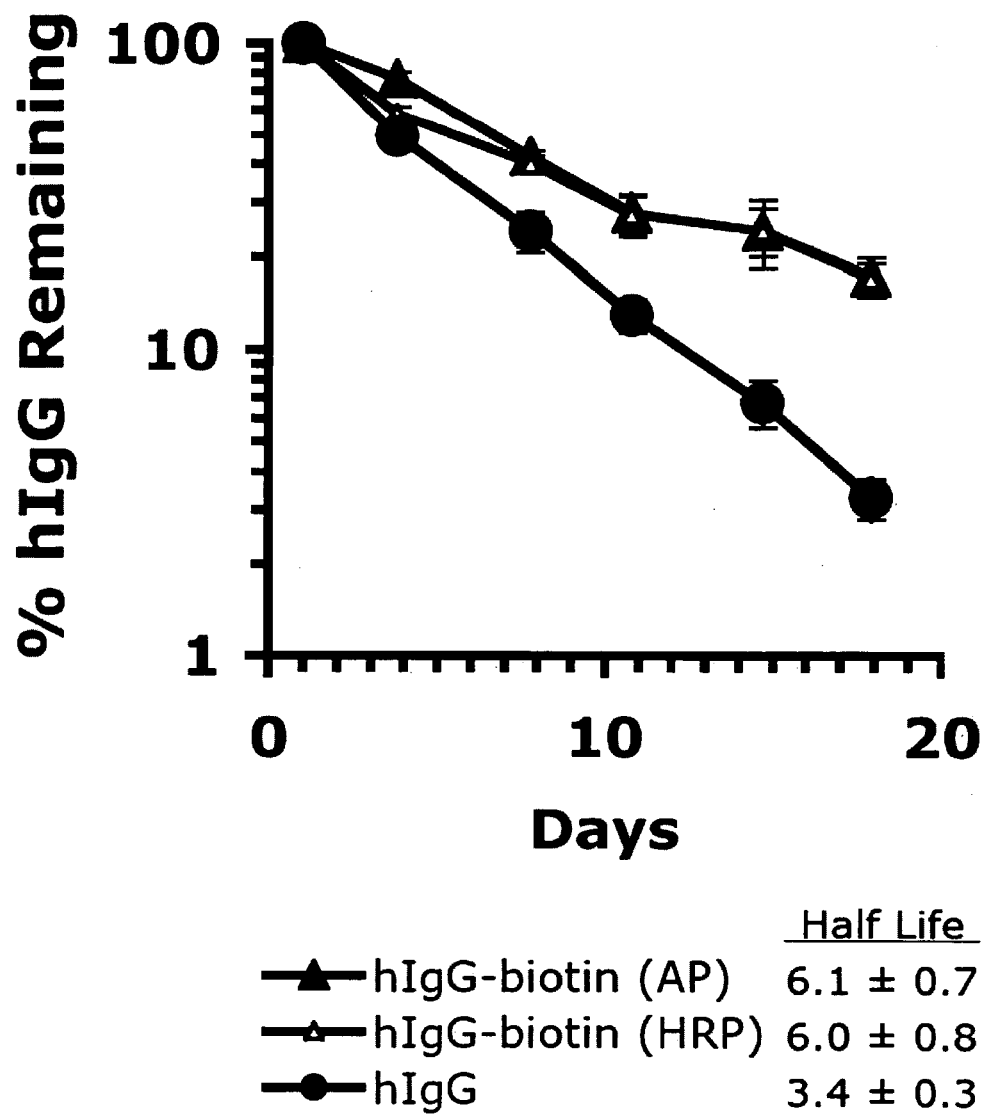
FIG. 2 shows determination of the plasma half-life for biotinylated hIgG compared to unmodified hIgG. The C57BL/6 mFcRn−/− hFcRn +/Tg Line 276 transgenic mouse model expressing the human FcRn receptor while lacking the mouse FcRn receptor was used for the in vivo study. HIgG-biotin (AP) is the data obtained when biotinylated hIgG was assayed using mouse anti-human kappa-alkaline phosphatase (AP); hIgG-biotin (HRP) is the data obtained when biotinylated hIgG was assayed using streptavidin-horse radish peroxidase (HRP). hIgG is the non-biotinylated hIgG control. Both methods, AP and HRP, give comparable results with biotinylation the half-life is extended to 6 days versus 3 days for unmodified hIgG.

Using either method for the ELISA, a) detection of biotinylated hIgG via its kappa chain (using mouse anti-human kappa-AP), or b) via the biotin group (SAv-HRP), the curves obtained for hIgG-biotin are identical and show increased protection observed for hIgG-biotin when compared to hIgG. This demonstrates that biotinylation of hIgG increases its plasma half-life (see FIG. 1 and FIG. 2).

Example 3

Correlation of Degree of Biotinylation to Plasma Half-life

To determine what degree of biotin conjugation was necessary to effect an increased half life, hIgG was labeled as described in Example 1, but with the reaction performed on ice to slow the rate to allow more precise labeling ratios, and the length of reaction was varied to obtain the biotin:hIgG ratios 1.2, 2.4, 4.6, and 7.2. As a model to analyze the plasma half life in vivo, we have used a mouse model expressing the human FcRn while lacking the mouse FcRn receptor on the C57BL/6 background (C57BL/6 FcRn−/−; hFcRn Tg276), which is described in (Petkova et al., 2006a). 100 μg of each of these hIgG-biotin tracers and hIgG were intraperitoneally injected into C57BL/6 mFcRn−/− hFcRn +/Tg Line 276 mice (5 mice/group) at day-3. Plasma was collected from mice on day 0, 7, 14, 21, and 28, and measured by hIgG ELISA as described in Example 2.

Figure 3:
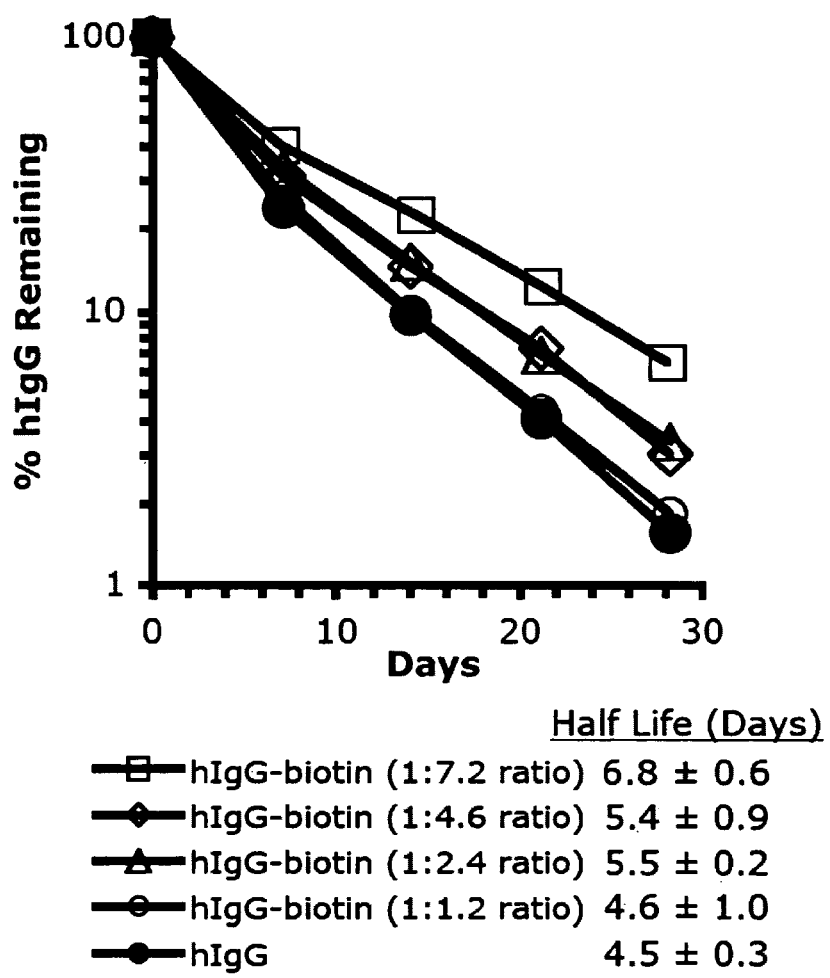
FIG. 3 shows determination of the plasma half-life of hIgG dependent of biotin:hIgG ratio. The C57BL/6 mFcRn−/− hFcRn +/Tg Line 276 transgenic mouse model expressing the human FcRn receptor while lacking the mouse FcRn receptor was used for the in vivo study. The figure shows that on average two biotin molecules per IgG is needed to increase half-life and that half-life is increased with additional biotin molecules per IgG molecule.

The conjugation of biotin to available lysine residues on hIgG increased this tracer's half-life in a dose dependent manner. When spread over all available lysine residues on hIgG, 2.4 biotin molecules per hIgG was the minimum number necessary to observe a significant increase in half-life compared to hIgG (p=0.012) as shown in FIG. 3.

Example 4

Figure 4:
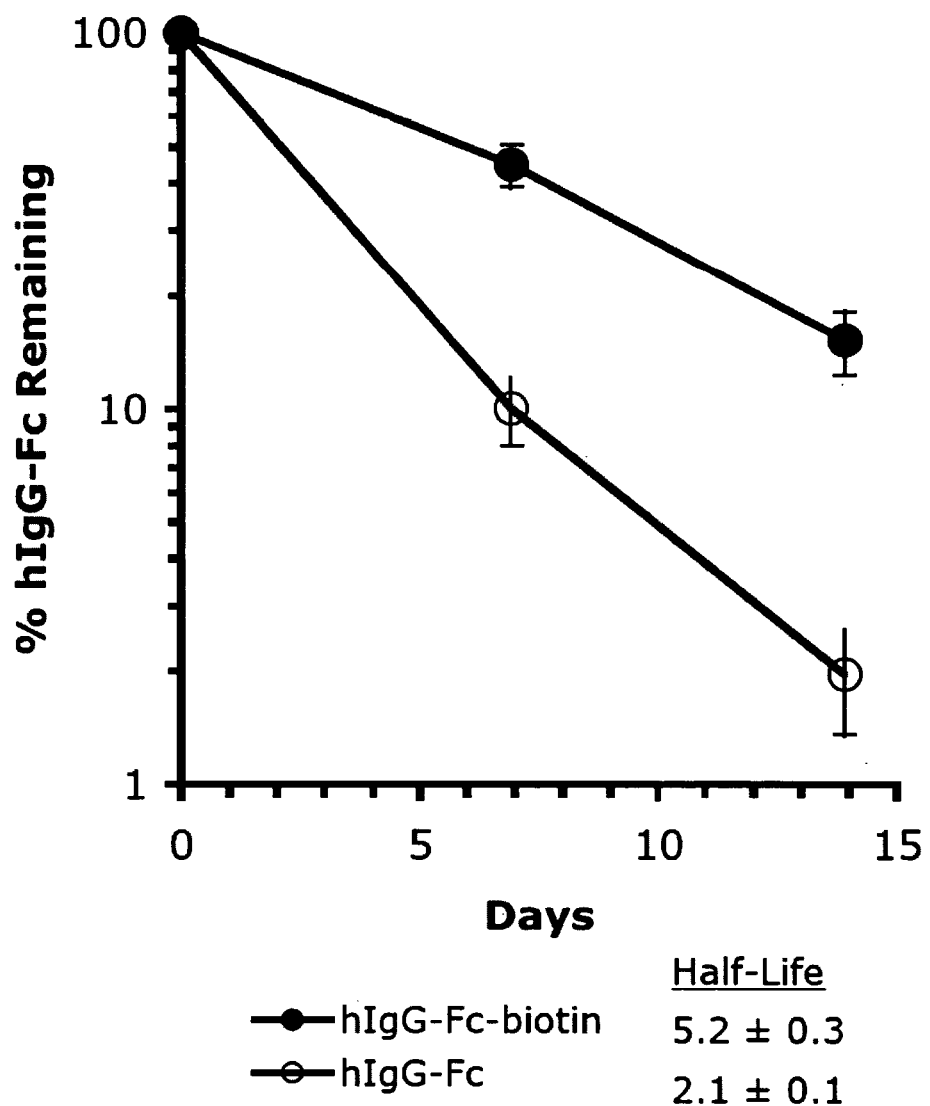
FIG. 4 shows determination of the plasma half-life biotinylated hIgG-Fc fragment (hIgG-Fc-biotin) compared to the unmodified Fc fragment (hIgG). The C57BL/6 mFcRn−/− hFcRn +/Tg Line 276 transgenic mouse model expressing the human FcRn receptor while lacking the mouse FcRn receptor was used for the in vivo study. This figures shows that biotin conjugated to the Fc fragment can increase the half-life of such by more than 2-fold.
Figure 5:
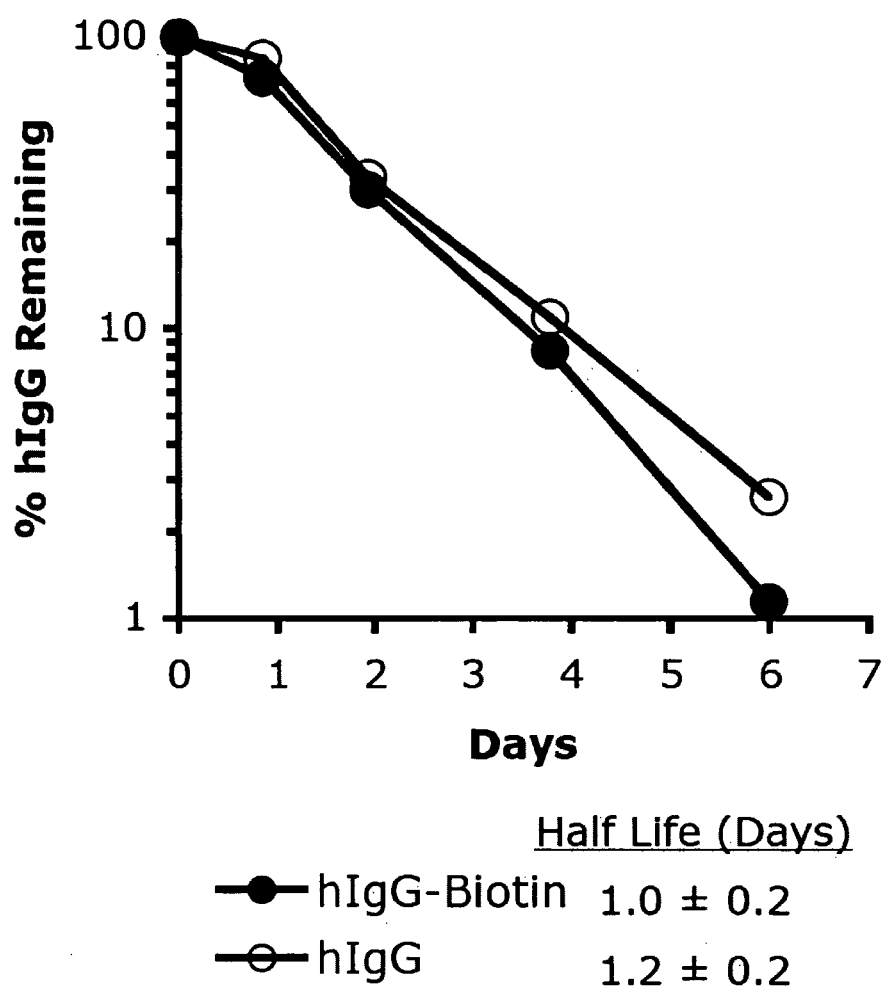
FIG. 5 shows that extension of plasma half-life is dependent on the FcRn receptor. Biotinylated hIgG and unmodified hIgG was injected into C57BL/6J FcRn−/− mice and the plasma half-life was determined. No difference between biotinylated hIgG and unmodified hIgG was detected.
Figure 6:
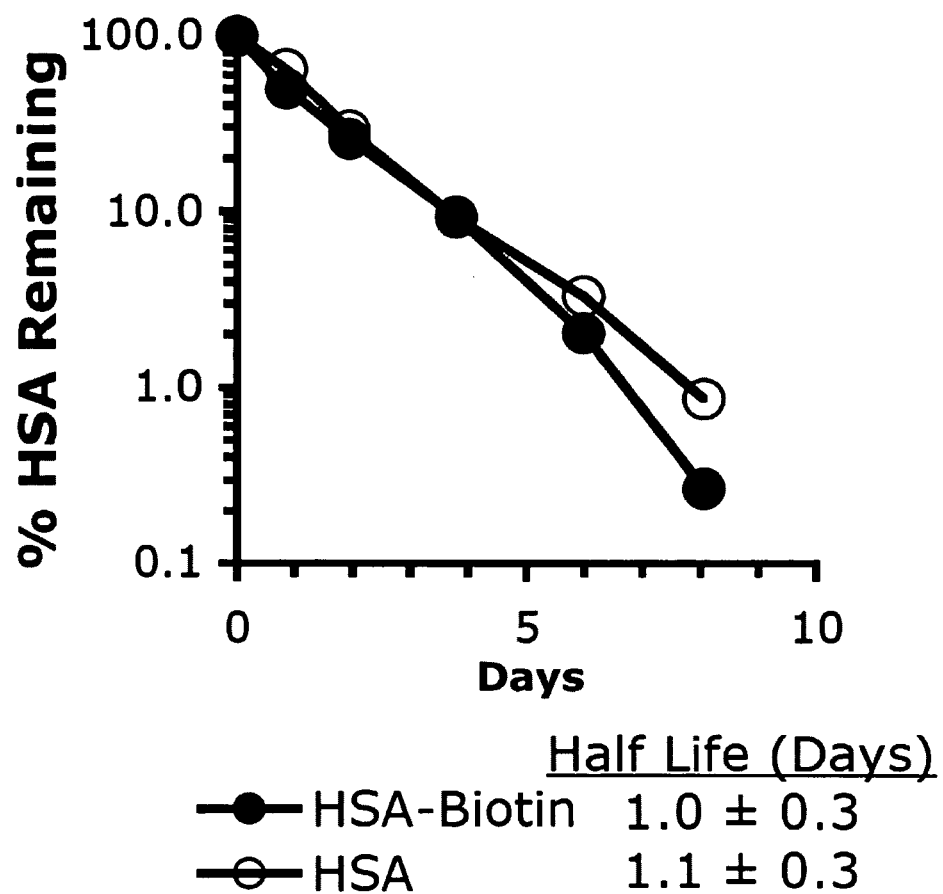
FIG. 6 shows analysis of plasma half-life of human serum albumin (HSA) to biotinylated human serum albumin (HSA-Biotin). The C57BL/6 mFcRn−/− hFcRn +/Tg Line 276 transgenic mouse model was used for the in vivo study. Biotinylation did not alter the half-life of human serum albumin.

Comparison of Biotinylation of Fc Fragment to hIgG hIgG Fc (Bethyl Laboratories cat. # P80-204) was biotin conjugated as described in Example 1 at room temperature for 30 minutes. The biotin:hIgG Fc ratio was quantified to be 6.2 using the method described in Example 3 assuming that the hIgG Fc fragment has a molecular weight equal to 50,000 g/mol. 100 μg of hIgG Fc-biotin, or hIgG Fc tracers were intraperitoneally injected into C57/BL6 mFcRn−/− hFcRn +/Tg Line 276 mice (5 mice/group) at day-3. Plasma was collected from mice and measured by hIgG ELISA as described in Example 2. hIgG Fc-biotin shows a longer plasma half-life than the hIgG Fc alone, indicating that lysines located on the Fc region of hIgG add to the protection of hIgG when biotinylated (see FIG. 4).

Example 5 hIgG-biotin Half-life Determination in the Absence of FcRn

Another approach to determining the mechanism for the increased half-life of hIgG-biotin compared to hIgG would be to manipulate the other side of the hIgG-FcRn equation. To accomplish this, hIgG-biotin and hIgG were used as tracers in C57BL/6 mFcRn−/− mice which lack both the mouse, and human FcRn (Roopenian et al., 2003). hIgG-biotin and hIgG Fc tracers were intraperitoneally injected into C57BL/6 mFcRn−/− mice (5 mice/group) at day-1. Plasma was collected from mice on day 0, 1, 2, 4, and 6 and measured by hIgG ELISA as described in Example 2.

In the absence of either human or mouse FcRn to protect the hIgG tracers, the addition of biotin to hIgG did not augment the half-life of the hIgG-biotin. This suggests that biotin conjugated to hIgG, a ligand of FcRn, interacts with the hFcRn in such a way to increase its protection from the lysosomal degradation pathway.

Example 6

Comparison of Biotinylated Serum Albumin to Serum Albumin

Serum albumin is the only other ligand known to bind FcRn other than IgG. Therefore, it was determined if biotinylation of human serum albumin (HSA) extends its half-life. HSA (Sigma, >96% purity) was biotin conjugated as described in Example 1 at room temperature for 30 minutes. The biotin:HSA ratio was quantified to be 6.6 using the method described in Example 1. To determine the half-life, 1 mg of HSA-biotin and HSA tracers were intraperitoneally injected into C57BL/6 mFcRn−/− hFcRn +/Tg Line 276 mice (5 mice/group) at day-1. Plasma was collected from mice on day 0, 1, 2, 4, 6, and 8 and measured by HSA ELISA.

An HSA ELISA was performed by coating ELISA plates with rabbit anti-human albumin (US Biological cat. # A1327-46) that was diluted to 0.5 µg/100 µl in 50 mM sodium bicarbonate buffer, pH 9.6 and incubated overnight at 4° C. Plates were hand washed 2 times 300 µl per well using DPBS with 0.05% Tween 20 and 0.05% sodium azide (ELISA Wash). Wash was removed by flicking plates into a sink and blotting the plates on paper towels. Plates were blocked with 300 µl/well of ELISA Block (ELISA Wash with 1% bovine serum albumin (BSA, Sigma cat. # A7284)) for a minimum of 1 hour at room temperature. Plasma samples were diluted 1/200 and 1/800 with diluent. HSA and HSA-biotin were diluted 2-fold from 1000 ng/ml down to 1 ng/ml to act as standards. Block was removed by flicking and blotting as before. 100 µl of diluted standards and plasma as well as diluent only (to act as blanks) were transferred into the coated and blocked ELISA plates. Plates were incubated at 37° C. for 1 hour, then washed as before 3 times 300 µl/well. Added 100 µl/well of goat anti-human HSA-AP (Bethyl Laboratories cat. # A80-229AP) diluted 1/200 in diluent and incubated at 37° C. for 1 hour, then washed as before 3 times 300 µl/well. Added 100 µl/well of 1 mg/ml p-nitrophenyl phosphate (Sigma Cat. # N2765) in Substrate Buffer. Read $A_{405\ nm}$ at 30 minutes, or when the maximum optical density exceeded 1. Data is plotted as the percent tracer remaining compared to the day 0 plasma tracer concentration. Biotinylation does not alter the half-life of HSA in vivo.

Example 7

Biotin and not the Spacer Increases the Half-life of IgG

Figure 12:
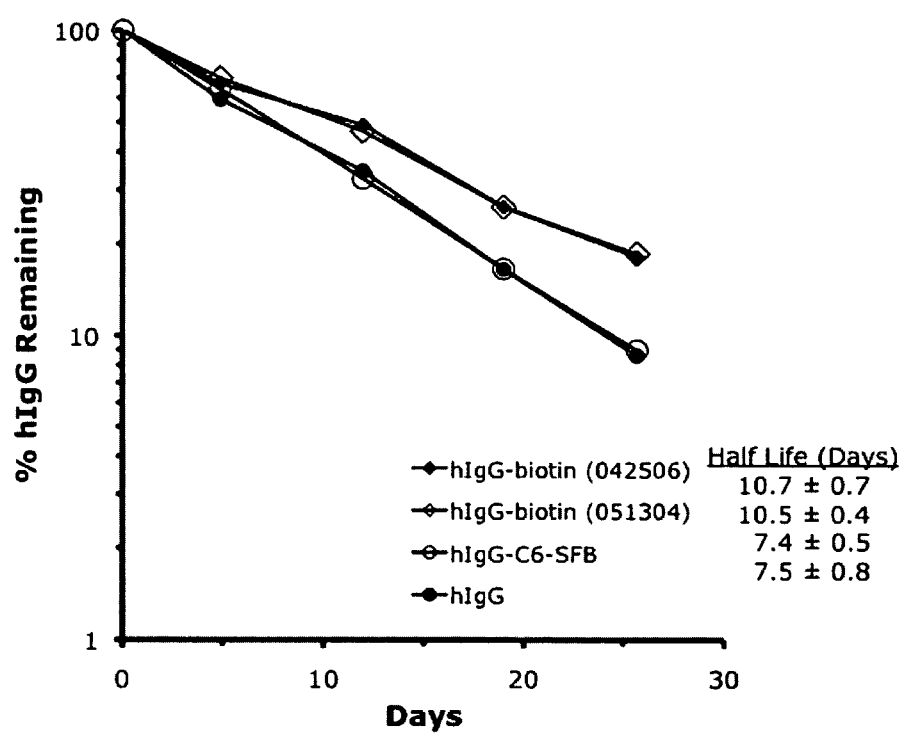
FIG. 12 shows biotin as a functional molecule. Human IgG (hIgG) was conjugated to biotin using NHS-biotin (biotin) or to C6-succinimidyl 4-formylbenzoate (C6-SFB) without biotin, as a similarly sized spacer moiety. The C57BL/6 mFcRn−/− hFcRn +/Tg Line 276 transgenic mouse model expressing the human FcRn receptor while lacking the mouse FcRn receptor was used for the in vivo study. HIgG was derivatized with NHS-biotin (HuIgG-biotin; open squares and filled squares) or with C6-SFB (HuIgG-SF-6; open circles) or not biotinylated (HuIgG; filled circles) and the half-life was determined. Two separately derivatized biotin preparations were used (042506 and 051304). Only biotinylation improved the half-life, about 1.4-fold compared with untreated hIgG and C6-SFB treated hIgG.

Biotinylation was conventionally applied using N-hydroxysuccinimidobiotin (NHS-biotin) chemistry in which the NHS-ester reacts with primary amine and the epsilon amines of lysine. To investigate the importance of the biotin group, the half-life of NHS-biotin derivatized hIgG was compared to that of hIgG which was derivatized with C6-succinimidyl 4-formylbenzoate (C6-SFB). Biotin-NHS (Pierce cat. #20217) and C6-SFB (Pierce cat. #22423) have the same length of 13.5 Å. The NHS chemistry used for both reagents allows a conjugation to epsilon amines of lysine. C6-SFB does not contain biotin, but instead the ring structure 4-formylbenzoate (see FIG. 7). LC-biotin and C6-SFB were conjugated to hIgG in parallel using the same method used to conjugate biotin to hIgG as described in Example 1. After reacting hIgG with C6-SFB, it was dialyzed. A reductive amination reaction using ethanolamine and sodium cyanobromohydride converted the aldehyde reactive end of the spacer C6-SFB to an unreactive hydroxyl. After adding 10 µl ethanolamine (Sigma cat. # E9508) to half of the hIgG-C6-SFB (1.7 ml) to get 100 mM ethanolamine. In a hood while vortexing, 17 µl of 5 M sodium cyanoborohydride in 1 M NaOH (Sigma cat. #296945) were added and incubated for 15 minutes at room temperature. The sample was dialyzed, again, and sterile filtered. The biotin conjugate had its biotin:hIgG ratio measured using the same method in Example 1, resulting in a ratio of 7.6. These hIgG conjugated tracers and unconjugated hIgG were intraperitoneally injected into C57BL/6 mFcRn−/− hFcRn +/Tg Line 276 mice (5 mice/group) at day-3. Plasma was collected from mice and measured by hIgG ELISA as described in Example 2. FIG. 12 shows that hIgG-C6-SFB, with the same overall length as biotin, but lacking a biotin moiety, did not alter the half-life when compared to hIgG, suggesting that the biotin moiety is important for the induced enhancement of hIgG half-life.

Example 8

Influence of Spacer on the Half-life of Biotinylated IgG

Figure 7:
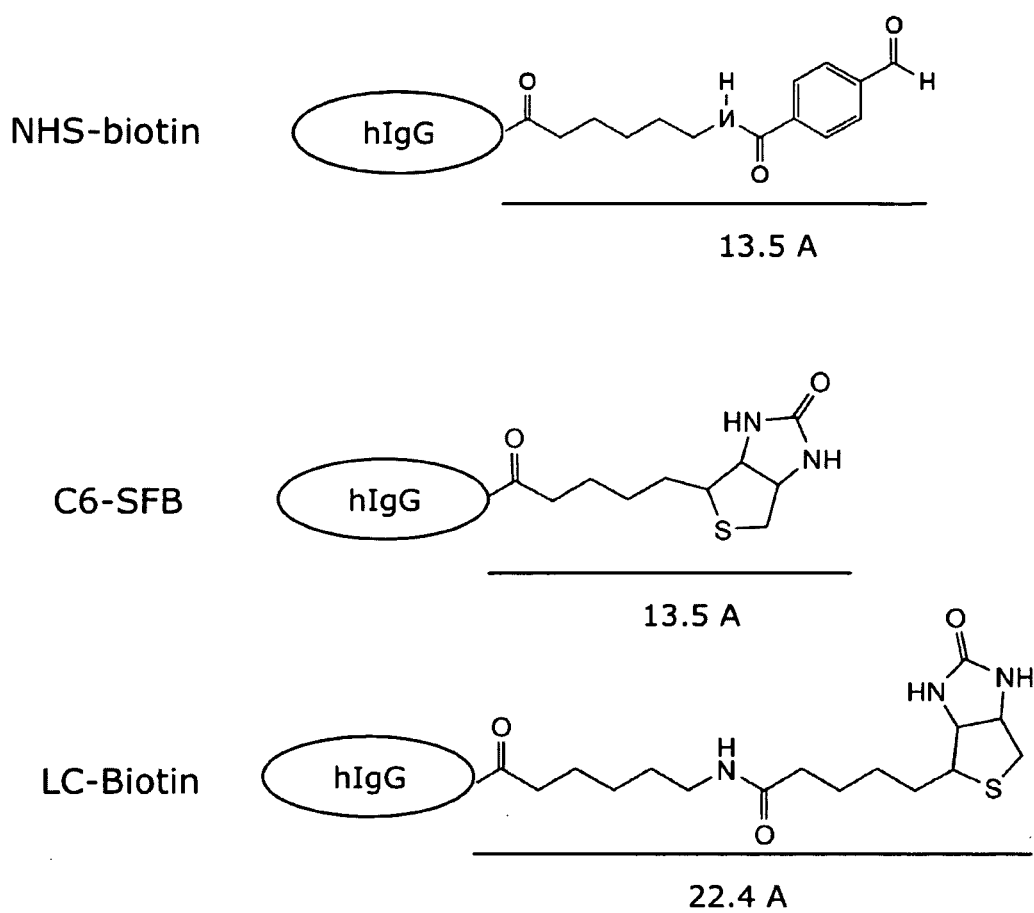
FIG. 7 depicts hIgG conjugated to biotin using NHS-biotin (NHS-biotin) or NHS-LC-biotin (LC-biotin). Further, the structure for C6-succinimidyl 4-formylbenzoate (C6-SFB) is shown, which is described in Example 7.
Figure 8:
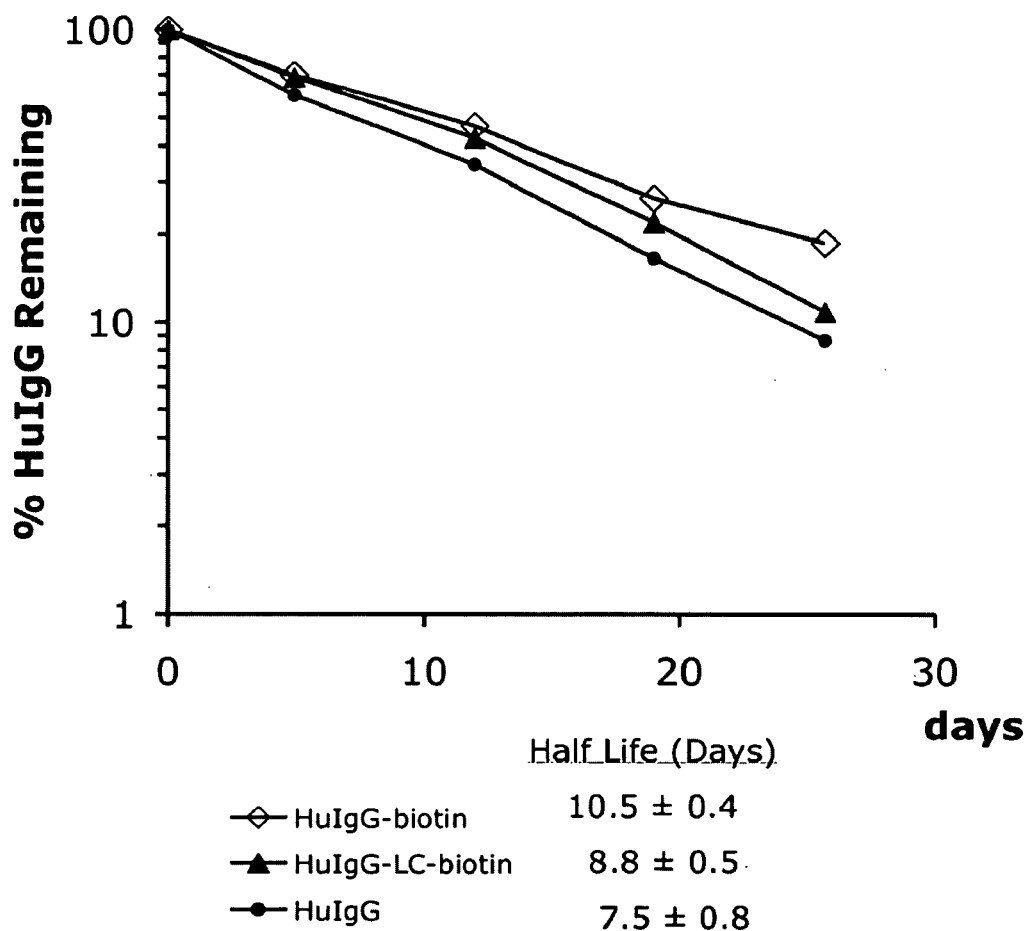
FIG. 8 shows plasma half-life analysis of different biotin spacers. The C57BL/6 mFcRn−/− hFcRn +/Tg Line 276 transgenic mouse model was used for the in vivo study. HIgG was biotinylated with NHS-biotin (HuIgG-biotin; open squares) or with NHS-LC biotin (HuIgG-LC-biotin; filled triangles) or not biotinylated (HuIgG; filled circles) and the half-life was determined. Both NHS-biotinylation moieties improved the half-life of hIgG.

Two spacers were compared, N-hydroxysuccinimidobiotin (NHS-biotin) and NHS-LC-biotin (Pierce cat. #21336) and see FIG. 7. NHS-biotin is 13.5 Å and for NHS-LC-biotin 22.4 Å long. The conjugation to human IgG (hIgG) was performed as described in Example 1 and the biotin:hIgG ratio for both linkers was approximately 7.6. These hIgG conjugated tracers and unconjugated hIgG were intraperitoneally injected into C57BL/6 mFcRn−/− hFcRn +/Tg Line 276 mice (5 mice/group) at day-3. Plasma was collected from mice and measured by hIgG ELISA as described in Example 2. When calculating the half-life hIgG-biotin yielded 10.5 days versus hIgG-LC-biotin 8.8 days versus the unconjugated hIgG control with 7.5 days (see table 1 and FIG. 8). This shows that with both spacers an improved half-life can be achieved, with the shorter spacer performing better.

TABLE 1

| Measurement of half-life in the C57BL/6 mFcRn−/−hFcRn +/Tg Line 276 mouse model ||
| --- | --- |
| IgG type | Half-life (days) |
| hIgG | 7.5 |
| hIgG-LC-biotin (NHS-LC-biotin) | 8.8 |
| hIgG-biotin (NHS-biotin) | 10.5 |

Example 9

Determination of hIgG1 Half-life with Biotin Conjugation

Figure 9:
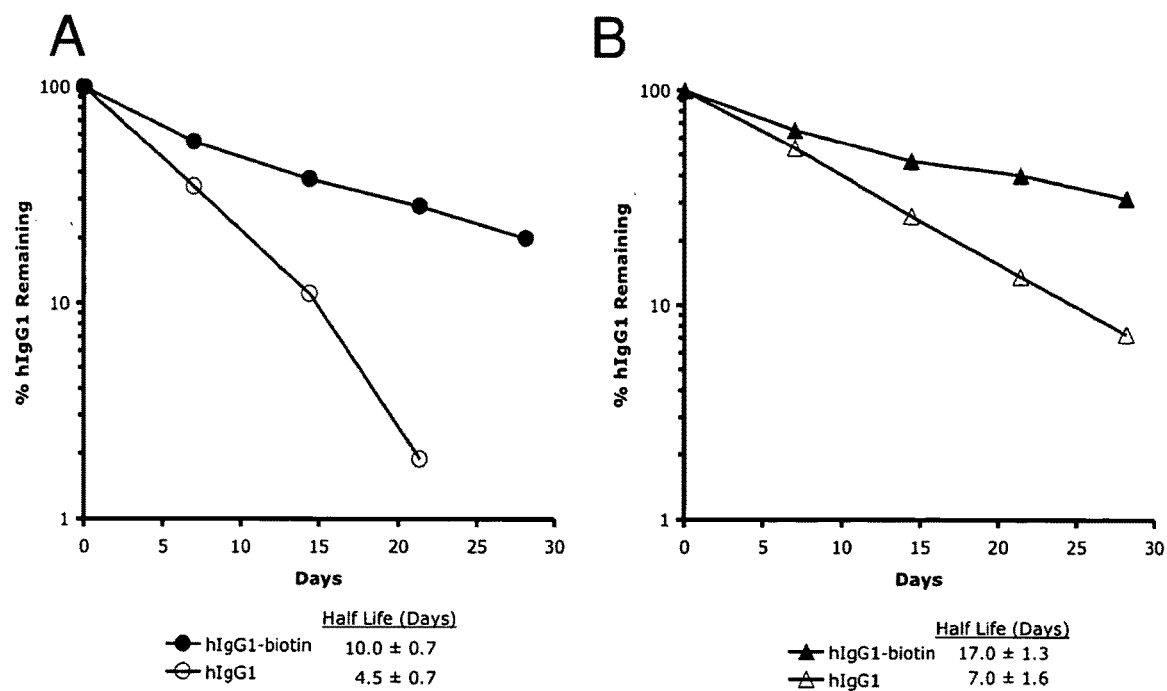
FIG. 9 shows half-life analysis of hIgG1 with, and without biotin conjugation. The C57BL/6 mFcRn−/− hFcRn +/Tg Line 276 transgenic mouse model expressing the human FcRn receptor while lacking the mouse FcRn receptor was used for the in vivo study. HIgG was biotinylated with NHS-biotin (hIgG1-biotin; filled circles) or not biotinylated (hIgG1; open circles) and the half-life was determined. Biotinylation increased the half-life by 2.2-fold. In panel A the effect of biotinylated hIgG1 is analyzed in C57BL/6 mFcRn−/− hFcRn +/Tg Line 276 transgenic mice carrying one copy of the human FcRn transgene and in panel B with two copies of the human FcRn transgene similarly showing that biotinylation of hIgG1 yields more than a two-fold increase in half-life in vivo.

Polyclonal hIgG-biotin and hIgG, prepared as described in Example 1, was intraperitoneally injected into hemizygous C57BL/6J mFcRn−/− hFcRn +/Tg Line 276 mice (5 mice/group) and homozygous C57BL/6J mFcRn−/− hFcRn Tg/Tg Line 276 mice (5 mice/group) at day-3. Plasma was collected from mice on day 0, 7, 14, 21, and 28, diluted 1/100, and measured by ELISA for hIgG1 as described in Example 1, except mouse anti-human IgG1Fc (Southern Biotech cat. #9052-01) was used at 1/200 dilution to capture, and hIgG1 (Calbiochem cat. #400120) was used as a standard. Biotinylation of hIgG1 extends the half-life of the hIgG1 portion of hIgG from 4.5±0.7 days to 10.0±0.7 days for the hemizygous and from 7.0±1.6 days to 17.0±1.3 days for the homozygous group as shown in FIG. 9.

Example 10

Determination of the Half-life of Biotinylated Mouse IgG1 In Vivo

Figure 10:
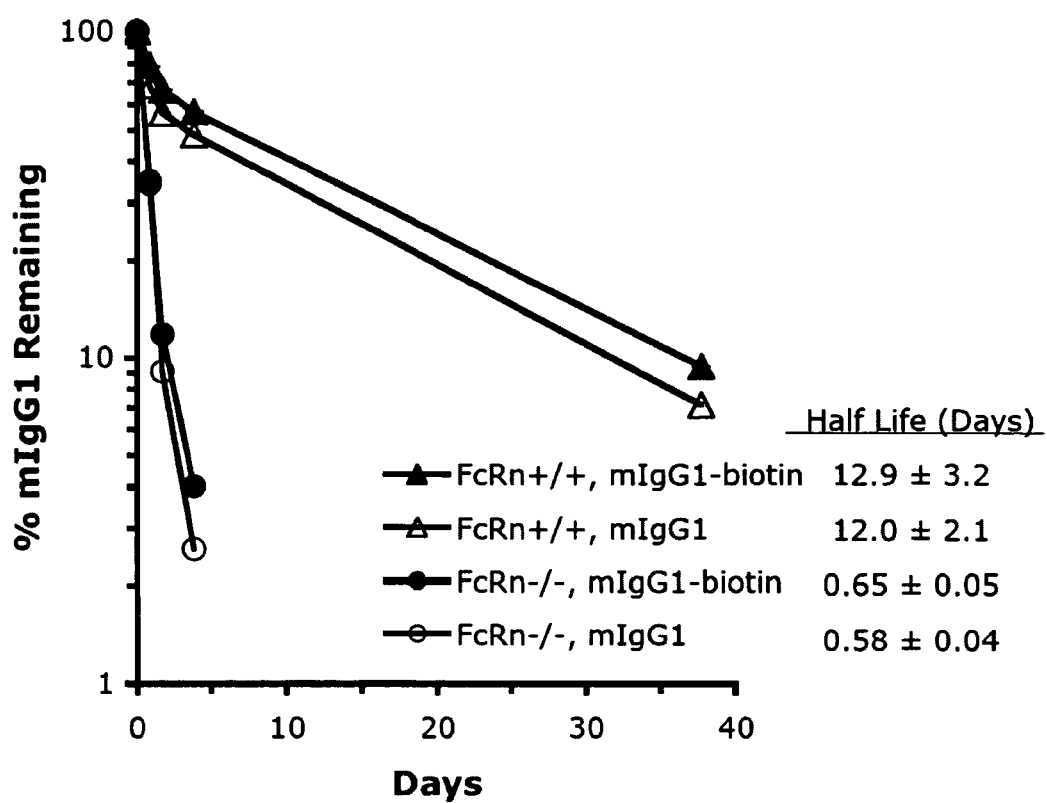
FIG. 10 shows half-life determination of mouse IgG1 (mIgG1) with (filled triangles or circles) and without (open triangles or circles) biotin conjugation in C57BL/6 J mice (triangles), and C57BL/6J mice lacking FcRn (circles). Biotinylation did not affect the half-life of mouse IgG1.

Mouse IgG1 (mIgG1) anti-DNP mAb (1B7.11: Kimura et al. Immunology 1986, 59, 235-238) was Protein G purified from ascites, and biotin conjugated as described in Example 1 to yield a biotin:mIgG1 ratio of 4.6. To determine the in vivo half-life of mIgG1-biotin and mIgG1 tracers, 100 µg of either was intraperitoneally injected into C57BL/6J, or C57BL/6J mFcRn−/− mice (5 mice/group) at day-1. Plasma was collected from mice on day 0, 1, 2, 4, and 38 and measured by ELISA as described in Example 1, except that bovine gamma globulin-DNP (Calbiochem cat. #324111) was used at 0.5 µg/100 µl/well to capture, goat anti-mouse kappa-AP (Southern Biotech cat. #1050-04) was used at 1/1000 to detect, and mIgG1 (1B7.11), or mIgG1-biotin were used to standardize. Biotinylation of mIgG1 does not extend its half life when used as a tracer in either C57B/6J mFcRn−/−, or C57B/6J wild type mice. FIG. 10 shows that biotinylation does not improve the half-life when only murine FcRn receptor is present or if no FcRn receptor is present suggesting that biotin is involved in the interaction with the human but not the mouse FcRn receptor.

Example 11

Determination of Biotinylated hIgG1 Chimeric Antibody Half-life In Vivo

Figure 11:
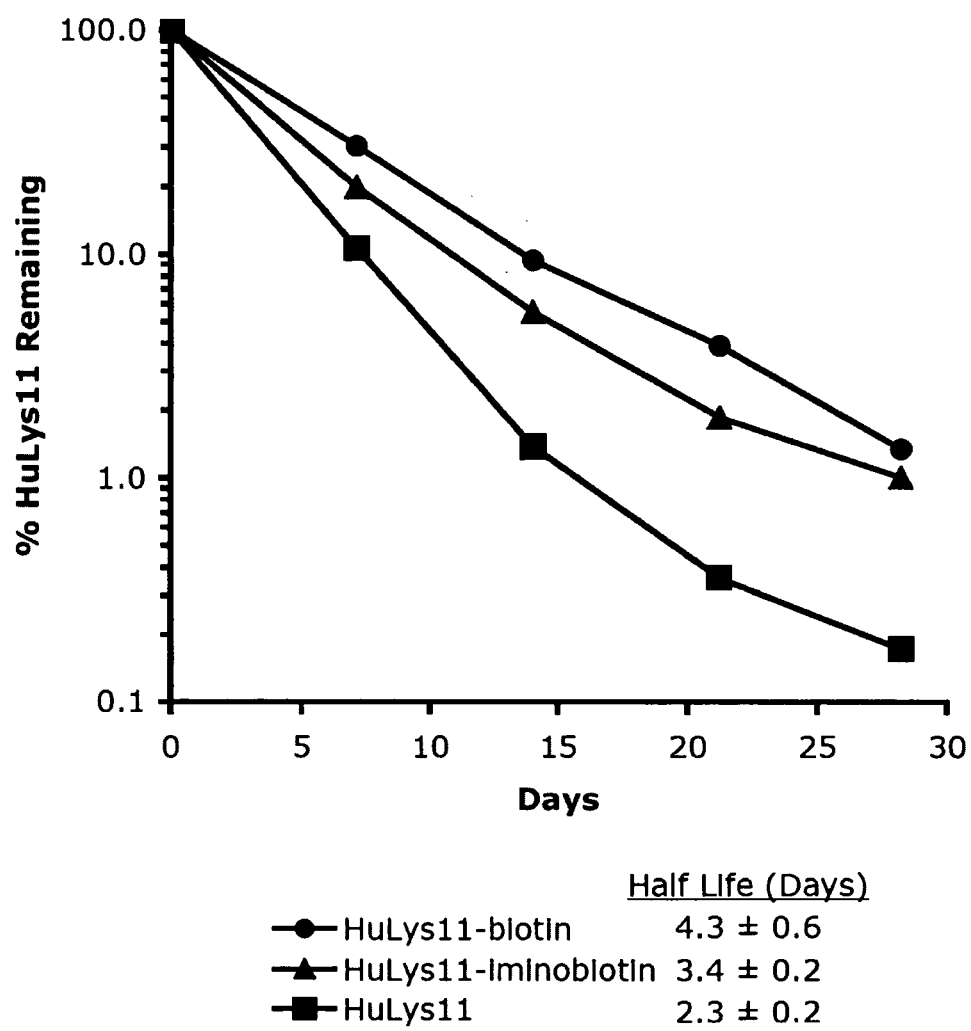
FIG. 11 shows that the biotin analog iminobiotin can extend the half-life of chimeric IgG1. The C57BL/6 mFcRn−/− hFcRn +/Tg Line 276 transgenic mouse model expressing the human FcRn receptor while lacking the mouse FcRn receptor was used for the in vivo study. The chimeric antibody HuLys11 was biotinylated with NHS-biotin (HuLys11-biotin; circles), with iminobiotin (HuLys11-iminobiotin, triangles) or not biotinylated (HuLys11; squares) and the half-life was determined. Biotinylation increased the half-life by 1.86-fold for HuLys11-biotin and 1.48-fold for HuLys11-iminobiotin compared to the unbiotinylated HuLys11 antibody.

We tested if biotinylation can extend the half life of human chimeric antibodies using the chimeric antibody HuLys11, as an example (Foote and Winter, 1992). HuLys11 is composed of a human IgG1Fc part and mouse heavy and light chain complementarity determining region (CDR) 1, 2, and 3 residues derived from the mouse mAb D1.3, which give the chimeric antibody its hen egg lysozyme (HEL) specificity. HuLys11 was biotinylated using the method described in Example 1. In a separate reaction, HuLys11 was also conjugated in parallel with a pH sensitive derivative of biotin called 2-iminobiotin, a cyclic guanidino analog of biotin. Iminobiotin binds streptavidin, like biotin, however it binds best at pH 9.5. As an example, only 2.5% of an iminobiotinylated protein (fetuin) bound to an avidin affinity column at pH 7.5, while 93% bound at pH 9.5 (Orr, 1981). The biotin:HuLy11 ratio was determined to be 4.5 using the method as described in Example 1. Due to iminobiotin preferentially binding to streptavidin at pH 9.5, or greater, the pH 7.5 buffers used to quantitate biotin in Example 1 would not allow accurate iminobiotin quantitation. An ELISA method similar to the one used in Example 2 was implemented to quantitate iminobiotin: HEL (Sigma cat. # L6876) at 0.5 µg/100 µl 150 mM sodium carbonate, pH 9.5 per well of the 96 well ELISA plate was used to capture, streptavidin-AP (Southern Biotech cat. #7100-04) diluted 1/1000 in 50 mM sodium carbonate, pH 9.5, 0.05% Tween 20, and 0.05% bovine serum albumin (BSA) was used to detect, and HuLys11-biotin was used as a standard. The ELISA plate was washed as described as described in Example 1, except 50 mM sodium carbonate, pH 9.5, with 0.05% Tween 20 was used as the wash buffer. HuLys11-iminobiotin was determined to have the same ratio as HuLys11-biotin:4.5. HuLys11-biotin, HuLys11-iminobiotin, and HuLys11 were intraperitoneally injected (100 µg/mouse) into C57BL/6 mFcRn−/− hFcRn +/Tg Line 276 mice (5 mice/group) at day-3. Plasma was collected from mice on day 0, 7, 14, 21, and 28, and measured using a modified ELISA similar to the method used in Example 2: HEL at 0.5 µg/100 µl PBS/well was used to capture, mouse anti-human kappa-AP was used to detect, and HuLys11 was used as a standard. Apparently due to the chimeric nature of HuLys11, this tracer had a half-life (2.3±0.2 days) that was significantly lower than the half-life determined for hIgG1 in Example 9 (4.5±0.7 days, p=0.001). Biotinylation significantly augmented the half-life of HuLys11 to 4.3±0.6 days (p=0.02). In spite of the high pH-dependent nature of iminobiotin binding to streptavidin, HuLys11-iminobiotin also had a half-life (3.4±0.2 days), which was significantly longer than for HuLys11 alone (p=0.00003) as shown in FIG. 11.

Example 12

Half-life Determination of Biotinylated Fc Fragment of Humanized hIgG1 Antibody In Vivo Herceptin (trastuzumab) is a humanized antibody carrying a hIgG1 Fc. To determine the effect of biotinylation on the half-life of this hIgG1 Fc fragment, the Fc fragment of Herceptin was purified, biotinylated, administered in vivo, and assayed by ELISA. 100 mg of Protein G purified Herceptin was digested in 20 mM sodium phosphate, pH 7.2, 10 mM EDTA, 20 mM cysteine using 5 ml of 50% immobilized papain slurry (Pierce Cat. #20341 with 0.25 mg papain/ml of gel) with Herceptin at 20 mg/ml (enzyme: substrate ratio of 1:160) for 4 hours at 37° C. with tube rotation. This preparation was centrifuged to recover digested Herceptin fragments as supernatant. The papain digested Herceptin was dialyzed against 10 mM sodium borate, pH 9.5 extensively. Herceptin fragments were diluted with 10 mM sodium borate, pH 9.5 (2 mg/ml protein), then added to 30 ml of regenerated DEAE-cellulose (Sigma D0909) that had been equilibrated with 10 mM sodium borate, pH 9.5. After rotation to mix for 1 hour, the DEAE-cellulose was centrifuged and the unbound fraction was discarded as F(ab)2. The DEAE-cellulose was exhaustively washed with 10 mM sodium borate, pH 9.5. The bound Herceptin Fc fragment was then eluted by adding 100 mM sodium citrate, pH 4.0. An Amicon Ultra-15 (Millipore UFC903024) was used to concentrate the Fc Fragment, which was then washed with 25 mM sodium phosphate, pH 7, and sterile filtered in preparation for injection. The Herceptin Fc fragment (>99% purity) was assessed by BCA protein assay to determine protein quantity, and by SDS-PAGE.

Figure 15:
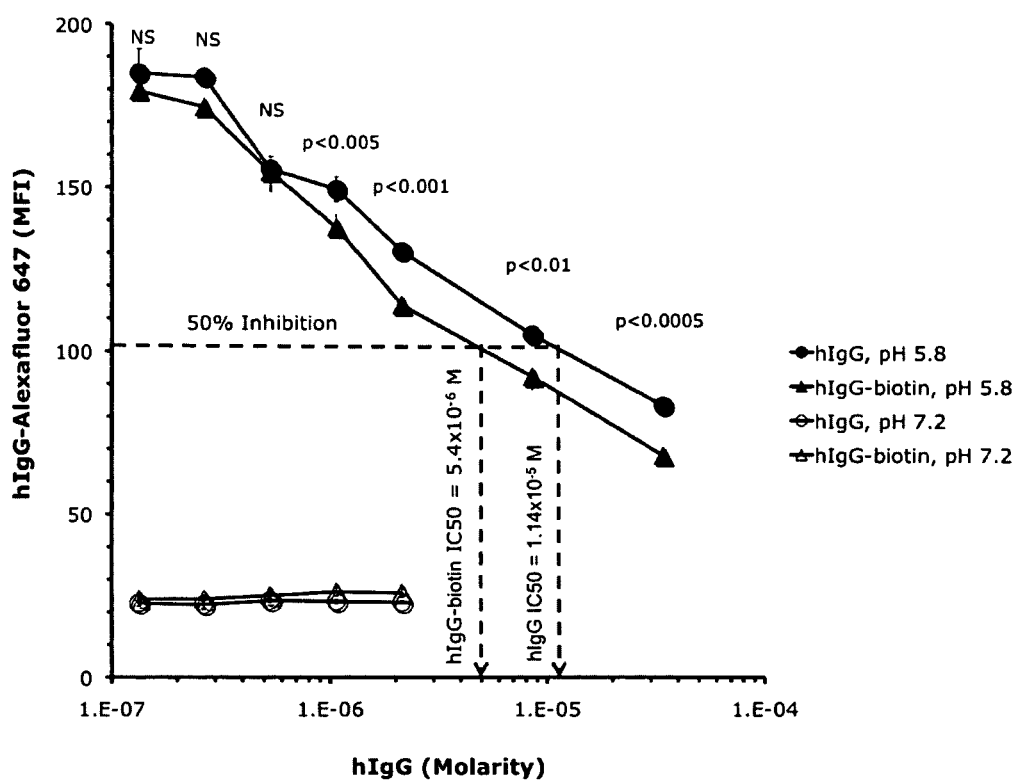
FIG. 15 shows results from a competitive binding assay in vitro investigating avidity of biotinylated and non-biotinylated hIgG to human FcRn.

The Herceptin Fc fragment was biotin conjugated as described in Example 1 at room temperature for 30 minutes. The biotin:hIgG1 Fc ratio was quantified to be 4.4 using the method described in Example 1, assuming that the Herceptin Fc fragment has a 50,000 molecular weight. 100 µg of Herceptin Fc-biotin, or unconjugated Fc tracers were intraperitoneally injected into C57/BL6 mFcRn−/− hFcRn +/Tg Line 276 mice (5 mice/group) at day-3. Plasma was collected from mice on day 0, 3, 7, 11, 14 and measured by hIgG ELISA as described in Example 2 with the exception that goat anti-human IgG-alkaline phosphatase (Southern Biotech 2040-04) diluted 1/1000 in diluent was used for detection. The results in FIG. 15 show that the unconjugated Herceptin Fc fragment half life (2.4±0.4) and biotinylated half life (5.6±1.3) were similar to the hIgG Fc fragment half life values and augmentation shown in Example 4.

Example 13

Determination if Biotinylation of hIgG Results Lowers the IC50 when Competing for Human FcRn Binding In Vitro It is known in the art that alterations in IgG antibodies that increase binding to FcRn in an acidic but not in a neutral pH environment can extend their half-life in vivo. Therefore, a primary mechanism, without wishing to be limited by a theory, which could explain the extension of the half-life of biotinylated hIgG is that the biotin modification enhances its binding avidity for hFcRn at an acidic pH. A flow-cytometry cell-based competitive binding assay, used successfully in the past, relies on binding labeled ligands to hFcRn on the plasma membrane, which should at least partially mimic the membrane dynamics of IgG/FcRn engagement in vivo. This cellular assay used the human 293 cell line that expresses a GFP-hFcRn construct lacking the endosomal targeting domain, thus diverting GFP-hFcRn expression to the plasma membrane (Petkova et al., 2006a). In a competitive binding assay, 5×105 cells/25 µl/test were incubated with a constant concentration of hIgG labeled with Alexa Fluor 647 (40 µg/ml), in competition with various concentrations (two fold serial dilutions from 320 µg/ml to 1.25 µg/ml, or 0 µg/ml) of biotinylated or unconjugated hIgG (competitors lacked a fluorescent label) in FACS buffer (PBS containing 1% BSA, 0.05% sodium azide) at pH 5.8, or 7.2 on ice for 2 hours. The cells were washed one time with 2 ml FACS Buffer at pH 5.8, or pH 7.2 and resuspended in 500 µl FACS buffer containing propidium iodide (0.2 µg/ml) to allow analysis of viable cells. Samples were analyzed for inhibition of binding of hIgG-Alexa Fluor 647 to hFcRn by competing hIgG using a FACSCalibur™ (BD Biosciences) flow cytometer. The Alexa Fluor 647 mean fluorescent intensity (MFI) of GFP gated events were plotted against competitor concentrations (FIG. 15). The MFI value at 50% inhibition was calculated from the formula:

MFI50% inhibition=(MFImax−MFImin)/2+MFImin where the MFImax is the MFI of cells at pH 5.8 with Alexa Fluor 647-hIgG without competitor and the MFImin is the MFI of cells at pH 7.2 with Alexa Fluor 647-hIgG at all competitor concentrations. The IC50 values were interpolated from the MFI value at 50% inhibition (102.7) to yield IC50 for hIgG-biotin (5.4×10-6 M) and hIgG (1.14×10-5 M) in FIG. 15. The results show that biotinylated hIgG has an approximate two fold decreased IC50 for hFcRn at an acidic pH 5.8, but not at a neutral pH 7.2 where no specific binding correlated to GFP intensity.

Example 14

Identification of Specific Biotinylated Lysine Residues in the Fc Fragment of the Chimeric Monoclonal Antibody HuLys11

The chimeric HuLys11 is comprised of a human IgG1Fc fragment and a mouse heavy and light chain complementarity determining region (CDR) 1, 2, and 3 (Foote and Winter, 1992). HuLys11 was biotinylated with the pH sensitive derivative of biotin, 2-iminobiotin, as described in Example 11 and functionally validated to confer a half-life extension as illustrated in FIG. 11. Mass spectrometry (MS) analysis was performed to identify the lysine residues of HuLys11 that are biotinylated by this method. 300 micrograms of iminobiotinylated HuLys11 was dialyzed against 50 mM ammonium bicarbonate, pH 9.5. This preparation was reduced by adding 12.5 µl 200 mM tributylphosphine in 1-methyl-2-pyrrolidone (TBP) from the ProteoPrep Reduction and Alkylation Kit (Sigma, Cat. # PROT-RA). The final concentration of TBP was 5 mM. This preparation was then incubated for 60 minutes at room temperature (RT), and then alkylated by adding 0.5 M iodoacetamide (15 mM final concentration) and incubated for 90 minutes at RT. The excess iodoacetamide was quenched the adding 200 mM tributylphosphine in 1-methyl-2-pyrrolidone and incubated for an additional 15 minutes at RT. Acetonitrile was then added to 4.5% v/v and HCl acidified trypsin was added to achieve a 1:40 trypsin to HuLys11-IB ratio. The samples were then digested by incubation at 37° C. overnight (~18 hours), and 50 mM ammonium bicarbonate, pH 9.5 was added to reduce the acetonitrile concentration to 1%. The trypsin digested HuLys11-IB samples were then transferred into tubes containing immobilized soybean trypsin inhibitor gel with 100× binding capacity to bind the trypsin, rotated to mix for 15 minutes at RT, centrifuged @ 2000 rpm for 2 minutes. The trypsin-depleted HuLys11-IB preparation was then transferred to a tube containing 0.1 ml of Streptavidin-Agarose gel with 2 mg Streptavidin (Sav) per ml gel that had been equilibrated with 50 mM ammonium bicarbonate, pH 9.5, incubated with mixing for 1 hour at RT, and centrifuged 2000 rpm for 2 minutes. The HuLys11-IB fragments bound to Sav-agarose were then washed consecutively with 1 ml per wash of 50 mM ammonium bicarbonate pH 9.5+0.2% NP40+2 mM EDTA+150 mM NaCl, then with 50 mM ammonium bicarbonate pH 9.5+0.2% NP40+2 mM EDTA+ 500 mM NaCl, and 5 times with 5 mM ammonium bicarbonate pH 9.5 to rid the SAv-agarose of nonspecifically bound proteins. The affinity purified HuLys11-IB fragments were then eluted by adding 5 mM citrate buffer, pH 2, rotated for 10 minutes at RT, and centrifuged 2000 rpm for 2 minutes.

The supernatant containing HuLys11-IB fragments were then submitted to the University of Massachusetts Medical School Mass Spectrometry Facility (on the world wide web at umassmed.edu/proteomic/index.aspx?linkidentifier=id&itemid=10552. Purified samples were analyzed by MALDI-TOF/TOF to identify an iminobiotin-derivatized tryptic fragments by both MS data from peptide mixtures as well as from Collisional-Induced-Dissociation (CID) analysis of individual peptides. The Mascot (on the world wide web at matrixscience.com) search algorithm generated several masses generated two masses (MR 2384 and 1491) that mapped to the HuLys11 heavy sequence. The sequence, FNWYVDGVEVHNAKTKPR (SEQ ID NO: 1), had an iminobiotin linkage to the position 288 lysine residue (underlined) and the second sequence, VSNKALPAPIEK (SEQ ID NO: 3), had its only lysine (underlined) in position 326 conjugated in the same manner. DNA sequence analysis of the HuLys11 clone and translation into the amino acid resulted in the following sequence:

```
                                       (SEQ ID NO: 18)
THTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLT

CLVKGFYPSDIAVEWESNGQPENNYKTTPPVLDSDGSFFLYSKLTVDK

SRWQQGNVFSCSVMHEALHNHYTQKSLSLSPGK.
```

Alignment of the peptide sequences (SEQ ID NO: 1 and SEQ ID NO: 3) to the Fc fragment of the HuLys11 amino acid sequence (SEQ ID NO: 18) reveal that both candidate lysine residues map to the Fc fragment and making them candidates for the increased plasma half-life. The first lysine residue is positioned lysine 288 and the second is positioned lysine 326, both based on amino acid nomenclature used in the application for the Fc domain is according to the EU index of Kabat et al., "Sequences of Proteins of Immunological Interest", 5th ed., National Institutes of Health, Bethesda, Md. (1991).

Example 15

Identification of Critical Lysine Residues for Biotinylation

To establish a direct cause and effect between candidate biotinylated lysine residues 288 and 326 of hIgG1 and an increase in plasma half-life in vivo, it is critical to functionally evaluate each candidate's role in extending the half-life of hIgG. To do so, two types of site-specific mutagenesis of the Fc gene candidate lysine codons can be performed: (1) elimination of the lysines; and (2) site-specific mutagenesis such that only one lysine residue is available for biotinylation.

(1) Elimination of candidate lysines. We have PCR cloned and sequence validated the HuLys11 heavy and light chains, which we have cloned into pcDNA 3.3-TOPO (heavy chain) and pOptiVEC-TOPO (light chain) vectors. Oligonucleotide-based mutagenesis can be employed to convert the candidate lysine residues 288 and 326 described above to arginine (R) by site specific mutagenesis using standard techniques known in the art. Arginine was chosen because it is similar in charge and size to lysine, but cannot be derivatized with NHS-biotin because it lacks an epsilon amine. The mutated heavy chains in the pcDNA 3.3-TOPO mammalian expression vector can then be transfected into CHO cells in combination with the pOptiVEC-TOPO (light chain) vector. Mutant and wild type HuLys11 antibodies isolated from the transfected CHO culture supernatant can then be protein G column purified.

To determine whether the lysine to arginine-substituted amino acids alter the in vivo half-life of HuLys11 antibodies, purified, mutant and wild type control HuLys11 antibodies can be conjugated with NHS-biotin or left unconjugated, and then administered to mFcRn−/− hFcRn transgenic mice. Serial serum samples can be analyzed by ELISA using hen egg lysozyme (HEL) as the capture ligand. Reduction in the half-life of NHS-biotinylated mutant variants as compared with the WT HuLys11 biotin conjugate would confirm the importance of the relevant lysine residue as causal to the biotin effect. Parallel experiments can be performed using the transplacental transfer assay described in Example 16. Furthermore, the same modified proteins can be evaluated for binding human FcRn in vitro as described in Example 13 to establish whether changes in half-life in vivo and avidity in vitro correlate.

Example 16

Determination if Biotinylation Improves the Therapeutic Efficacy of IVIg

Therapeutics benefits of high doses (1 g/kg) of IVIg have been attributed to the ability of IVIg to saturate the FcRn recycling pathway, resulting in the increased catabolic elimination of pathogenic endogenous antibodies (Curr Opin Immunol. 2007 December; 19(6):646-51. Epub 2007 Nov. 26; J Clin Invest. 2005 December; 115(12):3440-50. Epub 2005 Nov. 10; J Clin Invest. 2004 May; 113(9):1328-33; J Pharm Sci. 2007 June; 96(6):1625-37. Commercially available GammaGard® (Baxter Labs) are conjugated with NHS-biotin, or unconjugated, after its hIgG fraction has been isolated by Protein G chromatography. Doses of NHS-biotinylated IVIg and unconjugated IVIg ranging from 1 (expected subsaturation) to 5 mg/G (expected saturation based on previous studies) body weight are then injected once into groups of 5 C57BL/6 mFcRn−/− hFcRn +/Tg Line 276 mice that have previously received a tracer dose of the anti-HEL HuLys11 hIgG1. Serum concentrations of the anti-HEL HuLys11 mAb from serial blood samples can be assayed by ELISA, and serum half lives determined. This experiment tests whether biotinylated IVIg is more efficient at promoting the clearance of the anti-HEL HuLys11 mAb tracer than unbiotinylated IVIg.

Figure 13:
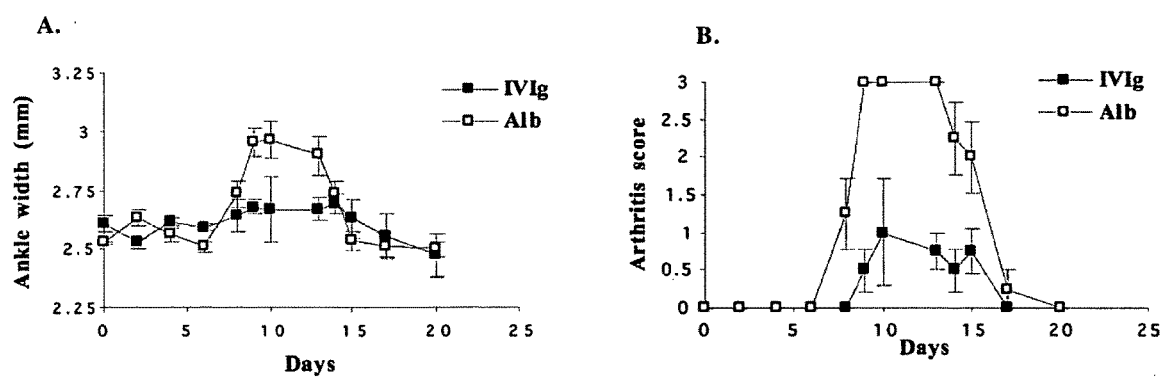
FIG. 13 shows that IVIg protects mice from ankle inflammation induced by serum from a rheumatoid arthritis patient. Groups of 3 Fcgr2b−/− mFcRn−/−hFcRn Tg Line 32 transgenic mice were injected on days 1, 3, 8 with 0.5 ml of arthritic serum and 1 G/Kg IVIg (IVIg) or human serum albumin (Alb) and monitored for ankle swelling and overall inflammation. IVIg treatment but not treatment with equivalent doses of human serum albumin resulted in the amelioration ankle swelling and overall inflammation.
Figure 14:
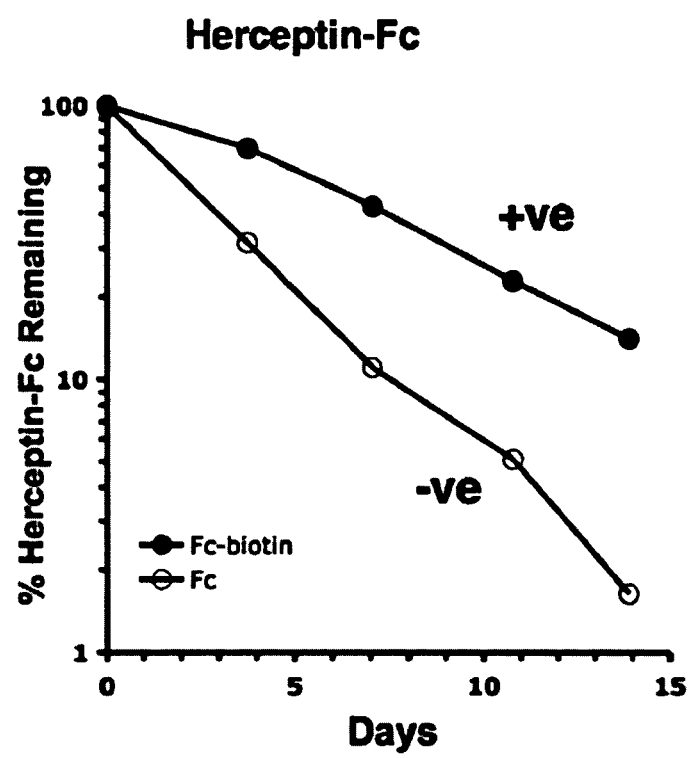
FIG. 14 shows the effect of biotinylation on serum half-life of the Fc fragment of the humanized monoclonal antibody Herceptin (trastuzumab) using the C57BL/6 mFcRn−/− hFcRn +/Tg Line 276 transgenic mouse model. The biotinylated purified human Fc fragment of Herceptin Hu4D5-IgG1 (filled circles) was analyzed in comparison to unbiotinylated antibodies (open circles) in the transgenic mouse model. In both cases, biotinylation results in an at least two-fold increase of half-life in vivo.

As a model for arthritis, the human arthritis serum transfer model described in Petkova et al 2006 (Petkova et al., 2006c) can be employed. In this model, serum (or purified IgG) from certain patients with rheumatoid arthritis caused transient arthritic episodes upon transfer into the Fcgr2b−/− mouse model. In this model, IVIg ameliorates the inflammatory effects of arthritic human serum when administered in saturating doses into Fcgr2b−/− mFcRn−/− hFcRn Tg 276 mice (FIG. 13). Groups of Fcgr2b−/− mFcRn−/− hFcRn Tg 276 mice treated with human arthritic serum from a preexisting pool of serum known to evoke robust ankle lesions are also administered limiting doses of biotinylated and unmodified control IVIg extrapolated from the above-described dosing experiment. Prior to treatment, the mice are injected with HuLys11 hIgG1 tracer, making it possible to monitor the overall effect of treatment on the serum hIgG half life. The mice are monitored for ankle width and for arthritis score (a combination of redness, swelling and overall inflammation) (Korganow et al., 1999; Petkova et al., 2006b). This experiment tests whether biotinylated IVIg more effectively confers anti-inflammatory effects compared with unbiotinylated IVIg.

Example 17

Determination if Biotinylation Improves Transplacental Transport of hIgG

The transplacental transport assay can be used to measure transcytosis of hIgG across the fetal trophoblast and the vascular endothelium (Al-Khabbaz, 2008). Pregnant C57BL/6 mFcRn−/− hFcRn +/Tg Line 276 mice are injected with 500 μg/mouse of biotinylated and un-conjugated hIgG diluted in 1×PBS to 200 μl/mouse total volume injected intraperitoneally at day 17 of gestation. Blood samples are collected from gestation stage day 19 and fetuses are collected. The level of biotinylated and unconjugated hIgG in the serum of both the mother and fetus can be determined by a standard sandwich ELISA.

Example 18

Determination of Whether Biotinylation is Additive with Other Types of Modifications Known to Enhance Half-lives and Transcytosis It is known in the art that the substitution of certain amino acids (e.g. the Hu4D5-IgG1 N434A) substantially increase the half-life; for example in human FcRn transgenic mice and non-human primates in (Dall'Acqua et al., 2006; Hinton et al., 2007; Hinton et al., 2006; Petkova et al., 2006a). Furthermore, it is known that such engineered antibodies can demonstrate enhanced transcytosis (Al-Khabbaz, 2008). To test if biotinylation results in synergistic or additive effects in combination with these defined amino acid modifications, variant antibodies with alanine replacements in key amino acids (e.g., IgG1 N434A) are biotinylated, as described in Example 1. To evaluate plasma half-lives in vivo, 100 µg of the biotinylated and un-conjugated variant antibody are compared. 100 µg of each antibody can be injected intraperitoneally into C57/BL6 mFcRn−/− hFcRn +/Tg Line 276 mice (5 mice/group) at day-3. Plasma can be collected serially from mice and the plasma concentrations of the injected antibodies are measured by ELISA as described in Example 2. The finding that the biotinylated version may show longer plasma half-life compared with the non-biotinylated version would be consistent with synergistic/additive effects. The same preparations can also be analyzed for transcytosis using the transplacental assay (see FIG. 15) to determine whether biotinylation acts synergistically with amino acid substitutions known to enhance transport.

REFERENCES

Al-Khabbaz, H. J. (2008). The role of the neonatal Fc receptor (FcRn) in the transfer of passive immunity and maintenance of active autoimmunity. In Biochemistry and Molecular Biology (Orono, The University of Maine).

Ali, S. A., Joao, H. C., Hammerschmid, F., Eder, J., and Steinkasserer, A. (1999). Transferrin trojan horses as a rational approach for the biological delivery of therapeutic peptide domains. J Biol Chem 274, 24066-24073.

Andersen, F. A. (2001). Final report on the safety assessment of Biotin. International Journal of Toxicology 20, 1-12.

Anderson, C. L., Chaudhury, C., Kim, J., Bronson, C. L., Wani, M. A., and Mohanty, S. (2006). Perspective—FcRn transports albumin: relevance to immunology and medicine. Trends in Immunology 27, 343-348.

Ashkenazi, A., and Chamow, S. M. (1997). Immunoadhesins as research tools and therapeutic agents. Current Opinion in Immunology 9, 195-200.

Bayer, E. A., and Wilchek, M. (1990). Protein biotinylation. Methods in Enzymology 184, 138-160.

Carter, P. J. (2006). Potent antibody therapeutics by design. Nature Reviews Immunology 6, 343-357.

Chapman, A. P. (2002). PEGylated antibodies and antibody fragments for improved therapy: A review. Advanced Drug Delivery Reviews 54, 531-545.

Chaudhury, C., Mehnaz, S., Robinson, J. M., Hayton, W. L., Pearl, D. K., Roopenian, D. C., and Anderson, C. L. (2003). The major histocompatibility complex-related Fc receptor for IgG (FcRn) binds albumin and prolongs its lifespan. Journal of Experimental Medicine 197, 315-322.

Dall'Acqua, W. F., Kiener, P. A., and Wu, H. (2006). Properties of Human IgG1s engineered for enhanced binding to the neonatal Fc Receptor (FcRn). Journal of Biological Chemistry 281, 23514-23524.

Dennis, M. S., Zhang, M., Meng, Y. G., Kadkhodayan, M., Kirchhofer, D., Combs, D., and Damico, L. A. (2002). Albumin binding as a general strategy for improving the pharmacokinetics of proteins. Journal of Biological Chemistry 277, 35035-35043.

Dickinson, B. L., Badizadegan, K., Wu, Z., Ahouse, J. C., Zhu, X., Simister, N. E., Blumberg, R. S., and Lencer, W. I. (1999). Bidirectional FcRn-dependent IgG transport in a polarized human intestinal epithelial cell line. Journal of Clinical Investigation 104, 903-911.

Duttaroy, A., Kanakaraj, P., Osborn, B. L., Schneider, H., Pickeral, O. K., Chen, C., Zhang, G., Kaithamana, S., Singh, M., Schulingkamp, R., et al. (2005). Development of a long-acting insulin analog using albumin fusion technology. Diabetes 54, 251-258.

Elliott, S., Lorenzini, T., Asher, S., Aoki, K., Brankow, D., Buck, L., Busse, L., Chang, D., Fuller, J., Grant, J., et al. (2003). Enhancement of therapeutic protein in vivo activities through glycoengineering. Nat Biotechnol 21, 414-421.

Foote, J., and Winter, G. (1992). Antibody framework residues affecting the conformation of the hypervariable loops. Journal of Molecular Biology 224, 487-499.

Frodin, J. E., Lefvert, A. K., and Mellstedt, H. (1990). Pharmacokinetics of the mouse monoclonal antibody 17-1A in cancer patients receiving various treatment schedules. Cancer Research 50, 4866-4871.

Ghetie, V., Popov, S., Borvak, J., Radu, C., Matesoi, D., Medesan, C., Ober, R. J., and Ward, E. S. (1997). Increasing the serum persistence of an IgG fragment by random mutagenesis. Nature Biotechnology 15, 637-640.

Ghetie, V., and Ward, E. S. (2000). Multiple roles for the major histocompatibility complex class I-related receptor FcRn. Annu Rev Immunol 18, 739-766.

Ghetie, V., and Ward, E. S. (2002). Transcytosis and catabolism of antibody. Immunol Res 25, 97-113.

Grubb, J. H., Vogler, C., Tan, Y., Shah, G. N., MacRae, A. F., and Sly, W. S. (2008). Infused Fc-tagged ?-glucuronidase crosses the placenta and produces clearance of storage in utero in mucopolysaccharidosis VII mice. Proceedings of the National Academy of Sciences of the United States of America 105, 8375-8380.

Haugland, R. P., and You, W. W. (1995). Coupling of monoclonal antibodies with biotin. Methods in molecular biology (Clifton, N.J.) 45, 223-233.

Haugland, R. P., and You, W. W. (1998). Coupling of antibodies with biotin. Methods in molecular biology (Clifton, N.J.) 80, 173-183.

Hinton, P. R., Tsurushita, N., Tso, J. Y., and Vasquez, M. (2007). Alteration of FcRn binding affinities or serum half-lives of antibodies by mutagenesis, US, ed. (US, PDL Biopharma, Inc).

Hinton, P. R., Xiong, J. M., Johlfs, M. G., Tang, M. T., Keller, S., and Tsurushita, N. (2006). An engineered human IgG1 antibody with longer serum half-life. Journal of Immunology 176, 346-356.

Jain, M., Kamal, N., and Batra, S. K. (2007). Engineering antibodies for clinical applications. Trends in Biotechnology 25, 307-316.

Junutula, J. R., Raab, H., Clark, S., Bhakta, S., Leipold, D. D., Weir, S., Chen, Y., Simpson, M., Tsai, S. P., Dennis, M. S., et al. (2008). Site-specific conjugation of a cytotoxic drug to an antibody improves the therapeutic index. Nat Biotech 26, 925-932.

Keyt, B. A., Paoni, N. F., Refino, C. J., Berleau, L., Nguyen, H., Chow, A., Lai, J., Pena, L., Pater, C., Ogez, J., et al. (1994). A faster-acting and more potent form of tissue plasminogen activator. Proc Natl Acad Sci USA 91, 3670-3674.

Kim, K. J., Fandy, T. E., Lee, V. H. L., Ann, D. K., Borok, Z., and Crandall, E. D. (2004). Net absorption of IgG via FcRn-mediated transcytosis across rat alveolar epithelial cell monolayers. American Journal of Physiology—Lung Cellular and Molecular Physiology 287.

Korganow, A. S., Ji, H., Mangialaio, S., Duchatelle, V., Pelanda, R., Martin, T., Degott, C., Kikutani, H., Rajewsky, K., Pasquali, J. L., et al. (1999). From systemic T cell self-reactivity to organ-specific autoimmune disease via immunoglobulins. Immunity 10, 451-461.

Levy, I., and Shoseyov, O. (2002). Cellulose-binding domains: Biotechnological applications. Biotechnology Advances 20, 191-213.

Lutz, J. F., and Boerner, H. G. (2008). Modern trends in polymer bioconjugates design. Progress in Polymer Science (Oxford) 33, 1-39.

Melder, R. J., Osborn, B. L., Riccobene, T., Kanakaraj, P., Wei, P., Chen, G., Stolow, D., Halpern, W. G., Migone, T. S., Wang, Q., et al. (2005). Pharmacokinetics and in vitro and in vivo anti-tumor response of an interleukin-2-human serum albumin fusion protein in mice. Cancer Immunology, Immunotherapy 54, 535-5475.

Mimura, Y., Church, S., Ghirlando, R., Ashton, P. R., Dong, S., Goodall, M., Lund, J., and Jefferis, R. (2000). The influence of glycosylation on the thermal stability and effector function expression of human IgG1-Fc: properties of a series of truncated glycoforms. Mol Immunol 37, 697-706.

Moses, J. E., and Moorhouse, A. D. (2007). The growing applications of click chemistry. Chemical Society Reviews 36, 1249-1262.

Ober, R. J., Radu, C. G., Ghetie, V., and Ward, E. S. (2001). Differences in promiscuity for antibody-FcRn interactions across species: Implications for therapeutic antibodies. International Immunology 13, 1551-1559.

Orr, G. A. (1981). The use of the 2-iminobiotin-avidin interaction for the selective retrieval of labeled plasma membrane components. Journal of Biological Chemistry 256, 761-766.

Osborn, B. L., Olsen, H. S., Nardelli, B., Murray, J. H., Zhou, J. X. H., Garcia, A., Moody, G., Zaritskaya, L. S., and Sung, C. (2002a). Pharmacokinetic and pharmacodynamic studies of a human serum albumin-interferon-alpha fusion protein in cynomolgus monkeys. Journal of Pharmacology and Experimental Therapeutics 303, 540-548.

Osborn, B. L., Sekut, L., Corcoran, M., Poortman, C., Sturm, B., Chen, G., Mather, D., Lin, H. L., and Parry, T. J. (2002b). Albutropin: A growth hormone-albumin fusion with improved pharmacokinetics and pharmacodynamics in rats and monkeys. European Journal of Pharmacology 456, 149-158.

Petkova, S. B., Akilesh, S., Sproule, T. J., Christianson, G. J., Al Khabbaz, H., Brown, A. C., Presta, L. G., Meng, Y. G., and Roopenian, D. C. (2006a). Enhanced half-life of genetically engineered human IgG1 antibodies in a humanized FcRn mouse model: Potential application in humorally mediated autoimmune disease. International Immunology 18, 1759-1769.

Petkova, S. B., Akilesh, S., Sproule, T. J., Christianson, G. J., Al Khabbaz, H., Brown, A. C., Presta, L. G., Meng, Y. G., and Roopenian, D. C. (2006b). Enhanced half-life of genetically engineered human IgG1 antibodies in a humanized FcRn mouse model: potential application in humorally mediated autoimmune disease. Int Immunol 18, 1759-1769.

Petkova, S. B., Konstantinov, K. N., Sproule, T. J., Lyons, B. L., Al Awwami, M., and Roopenian, D. C. (2006c). Human antibodies induce arthritis in mice deficient in the low-affinity inhibitory IgG receptor FcagammaRIIB. Journal of Experimental Medicine 203, 275-280.

Polakis, P. (2005). Arming antibodies for cancer therapy. Current Opinion in Pharmacology 5, 382-387.

Raju, T. S., and Scallon, B. (2007). Fc glycans terminated with N-acetylglucosamine residues increase antibody resistance to papain. Biotechnol Prog 23, 964-971.

Raju, T. S., and Scallon, B. J. (2006). Glycosylation in the Fc domain of IgG increases resistance to proteolytic cleavage by papain. Biochem Biophys Res Commun 341, 797-803.

Roopenian, D. C., and Akilesh, S. (2007). FcRn: the neonatal Fc receptor comes of age. Nat Rev Immunol 7, 715-725.

Roopenian, D. C., Christianson, G. J., Sproule, T. J., Brown, A. C., Akilesh, S., Jung, N., Petkova, S., Avanessian, L., Choi, E. Y., Shaffer, D. J., et al. (2003). The MHC class I-like IgG receptor controls perinatal IgG transport, IgG homeostasis, and fate of IgG-Fc-coupled drugs. Journal of Immunology 170, 3528-3533.

Sanchez, L. M., Penny, D. M., and Bjorkman, P. J. (1999). Stoichiometry of the interaction between the major histocompatibility-complex-related Fc receptor and its Fc ligand. Biochemistry 38, 9471-9476.

Schuck, P., Radu, C. G., and Ward, E. S. (1999). Sedimentation equilibrium analysis of recombinant mouse FcRn with murine IgG1. Molecular Immunology 36, 1117-1125.

Sinclair, A. M., and Elliott, S. (2005). Glycoengineering: The effect of glycosylation on the properties of therapeutic proteins. Journal of Pharmaceutical Sciences 94, 1626-1635.

Smith, B. J., Popplewell, A., Athwal, D., Chapman, A. P., Heywood, S., West, S. M., Carrington, B., Nesbitt, A., Lawson, A. D. G., Antoniw, P., et al. (2001). Prolonged in vivo residence times of antibody fragments associated with albumin. Bioconjugate Chemistry 12, 750-756.

Sung, C., Nardelli, B., Lafleur, D. W., Blatter, E., Corcoran, M., Olsen, H. S., Birse, C. E., Pickeral, O. K., Zhang, J., Shah, D., et al. (2003). An IFN-beta-albumin fusion protein that displays improved pharmacokinetic and pharmacodynamic properties in nonhuman primates. Journal of Interferon and Cytokine Research 23, 25-36.

Ugarova, N. N., Rozhkova, G. D., and Berezin, I. V. (1979). Chemical modification of the epsilon-amino groups of lysine residues in horseradish peroxidase and its effect on the catalytic properties and thermostability of the enzyme. Biochimica et biophysica acta 570, 31-42.

Umana, P., Jean-Mairet, J., Moudry, R., Amstutz, H., and Bailey, J. E. (1999). Engineered glycoforms of an antineuroblastoma IgG1 with optimized antibody-dependent cellular cytotoxic activity. Nat Biotechnol 17, 176-180.

Vaccaro, C., Zhou, J., Ober, R. J., and Ward, E. S. (2005). Engineering the Fc region of immunoglobulin G to modulate in vivo antibody levels. Nature Biotechnology 23, 1283-1288.

Veronese, F. M., and Pasut, G. (2005). PEGylation, successful approach to drug delivery. Drug Discovery Today 10, 1451-1458.

Vo, A A., Lukovsky, M., Toyoda, M., Wang, J., Reinsmoen, N. L., Lai, C. H., Peng, A., Villicana, R., Jordan, S. C. (2008) N Engl J. Med. 359(3), 242-251

Waldmann, T. A., and Strober, W. (1969). Metabolism of immunoglobulins. Prog Allergy 13, 1-110.

West A. P., J., and Bjorkman, P. J. (2000). Crystal structure and immunoglobulin G binding properties of the human major histocompatibility complex-related Fc receptor. Biochemistry 39, 9698-9708.

Wong, S. S. (1991). Chemistry of Protein Conjugation and Cross Linking (Boca Raton, Fla., USA, CRC-Press).

Wu, A. M., and Senter, P. D. (2005). Arming antibodies: prospects and challenges for immunoconjugates. Nat Biotech 23, 1137-1146.

Yeh, P., Landais, D., Lemaitre, M., Maury, I., Crenne, J. Y., Becquart, J., Murry-Brelier, A., Boucher, F., Montay, G., Fleer, R., et al. (1992). Design of yeast-secreted albumin derivatives for human therapy: Biological and antiviral properties of a serum albumin-CD4 genetic conjugate. Proceedings of the National Academy of Sciences of the United States of America 89, 1904-1908.

Yeo, D. S. Y., Srinivasan, R., Chen, G. Y. J., and Yao, S. Q. (2004). Expanded utility of the native chemical ligation reaction. Chemistry—A European Journal 10, 4664-4672.

Yoshida, M., Claypool, S. M., Wagner, J. S., Mizoguchi, E., Mizoguchi, A., Roopenian, D. C., Lencer, W. I., and Blumberg, R. S. (2004). Human neonatal Fc receptor mediates transport of IgG into luminal secretions for delivery of antigens to mucosal dendritic cells. Immunity 20, 769-783.

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of increasing the half-life of an IgG (immunoglobulin G) antibody in blood circulation in a human subject in need thereof, comprising the steps of:

(i) providing an IgG (immunoglobulin G) antibody preparation, said IgG antibody comprising a human Fc domain and said preparation comprising a biotinylated IgG antibody, wherein said IgG antibody is conjugated to biotin at a molar ratio of 2-10 biotin molecules per IgG antibody molecule;

(ii) administering to a human subject said IgG antibody preparation comprising an effective amount of said biotinylated IgG antibody, wherein said biotinylated IgG antibody binds to human FcRn via the constant region of said human Fc domain on said biotinylated IgG antibody to increase the half-life of said biotinylated IgG antibody in vivo, and (iii) maintaining said biotinylated IgG antibody in blood circulation over a period of days in said human subject, wherein said IgG antibody is covalently conjugated to biotin via a lysine amino acid residue at position 288 and/or 326, numbering according to EU index of Kabat, and wherein said biotin molecule is covalently conjugated to a solvent exposed lysine within the human Fc domain sequence selected from the group consisting of:

```
FNWYVDGVEVHNAKTKPR,      (SEQ ID NO: 1)

FKWYVDGVEVHNAKTKPR,      (SEQ ID NO: 2)
and

VSNKALPAPIEK.            (SEQ ID NO: 3)
```

2. The method of claim 1, wherein said IgG antibody is a monoclonal antibody.

3. The method of claim 1, wherein said IgG antibody is a humanized IgG antibody.

* * * * *